United States Patent
Curley et al.

(10) Patent No.: US 9,743,984 B1
(45) Date of Patent: Aug. 29, 2017

(54) DEVICES AND METHODS FOR DELIVERING FLUID TO TISSUE DURING ABLATION THERAPY

(71) Applicant: Thermedical, Inc., Waltham, MA (US)

(72) Inventors: Michael G. Curley, Weston, MA (US); Gregory R. Eberl, Acton, MA (US); Jason M. Clevenger, Needham, MA (US); Michael T. Howard, Dracut, MA (US); Erik Delly, Cambridge, MA (US)

(73) Assignee: Thermedical, Inc., Waltham, MA (US)

( * ) Notice: Subject to any disclaimer, the term of this patent is extended or adjusted under 35 U.S.C. 154(b) by 0 days.

(21) Appl. No.: 15/234,858

(22) Filed: Aug. 11, 2016

(51) Int. Cl.
A61B 18/18 (2006.01)
A61B 18/14 (2006.01)
A61B 18/00 (2006.01)

(52) U.S. Cl.
CPC ...... *A61B 18/1492* (2013.01); *A61B 2018/00577* (2013.01); *A61B 2018/00714* (2013.01); *A61B 2018/00744* (2013.01); *A61B 2218/002* (2013.01)

(58) Field of Classification Search
CPC .......... A61B 18/04; A61B 2018/00577; A61B 2018/00821; A61B 2018/046; A61B 18/082; A61B 18/1477; A61B 2017/00526; A61B 2018/00029; A61B 2018/00642; A61B 2018/00773; A61B 2018/00791;
(Continued)

(56) References Cited

U.S. PATENT DOCUMENTS

| 4,160,455 A | 7/1979 | Law |
| 4,424,190 A | 1/1984 | Mather, III et al. |
| 5,271,413 A | 12/1993 | Dalamagas et al. |

(Continued)

FOREIGN PATENT DOCUMENTS

| CN | 1119127 C | 8/2003 |
| CN | 1525839 A | 9/2004 |

(Continued)

OTHER PUBLICATIONS

Brace CL. Microwave tissue ablation: biophysics, technology, and applications.; Crit Rev Biomed Eng. 2010;38 (1):65-78.
(Continued)

*Primary Examiner* — Michael Peffley
*Assistant Examiner* — Amanda Zink
(74) *Attorney, Agent, or Firm* — Nutter McClennen & Fish LLP

(57) ABSTRACT

Devices and methods for delivering fluid to tissue during ablation therapy are described herein. An exemplary device can include an elongate body having an inner lumen, outlet ports, and an ablation element configured to heat tissue. A flow resistance of the elongate body can increase along a length of the elongate body containing the outlet ports in a proximal to distal direction. This can be accomplished by, for example, varying outlet port size or relative spacing, decreasing a cross-sectional area of the inner lumen through which fluid can flow using a flow diverter or tapered inner lumen sidewalls, or limiting a ratio between a total area of the outlet ports and a cross-sectional area of the inner lumen. Adjusting flow resistance of the elongate body can provide more uniform fluid distribution or a desired non-uniform distribution.

19 Claims, 21 Drawing Sheets

(58) Field of Classification Search
CPC ..... A61B 2018/00797; A61B 2018/00809; A61B 2018/1425
See application file for complete search history.

(56) References Cited

U.S. PATENT DOCUMENTS

| | | | |
|---|---|---|---|
| 5,336,222 A | 8/1994 | Durgin, Jr. et al. | |
| 5,403,311 A | 4/1995 | Abele et al. | |
| 5,409,487 A | 4/1995 | Jalbert et al. | |
| 5,431,648 A | 7/1995 | Lev | |
| 5,431,649 A | 7/1995 | Mulier et al. | |
| 5,437,673 A | 8/1995 | Baust et al. | |
| 5,449,380 A | 9/1995 | Chin | |
| 5,456,682 A | 10/1995 | Edwards et al. | |
| 5,458,597 A | 10/1995 | Edwards et al. | |
| 5,462,521 A | 10/1995 | Brucker et al. | |
| 5,472,441 A | 12/1995 | Edwards et al. | |
| 5,496,271 A | 3/1996 | Burton et al. | |
| 5,522,815 A | 6/1996 | Durgin, Jr. et al. | |
| 5,545,195 A | 8/1996 | Lennox et al. | |
| 5,549,559 A | 8/1996 | Eshel | |
| 5,653,692 A | 8/1997 | Masterson et al. | |
| 5,728,143 A | 3/1998 | Gough et al. | |
| 5,735,846 A | 4/1998 | Panescu et al. | |
| 5,800,482 A | 9/1998 | Pomeranz et al. | |
| 5,827,269 A | 10/1998 | Saadat | |
| 5,891,094 A | 4/1999 | Masterson et al. | |
| 5,891,134 A | 4/1999 | Goble et al. | |
| 5,954,719 A | 9/1999 | Chen et al. | |
| 5,964,791 A | 10/1999 | Bolmsjo | |
| 6,024,743 A | 2/2000 | Edwards | |
| 6,030,379 A | 2/2000 | Panescu et al. | |
| 6,032,077 A | 2/2000 | Pomeranz | |
| 6,045,549 A | 4/2000 | Smethers et al. | |
| 6,056,746 A | 5/2000 | Goble et al. | |
| 6,071,280 A | 6/2000 | Edwards et al. | |
| 6,080,151 A * | 6/2000 | Swartz | A61B 18/1492 606/45 |
| 6,112,123 A | 8/2000 | Kelleher et al. | |
| 6,119,041 A | 9/2000 | Pomeranz et al. | |
| 6,139,570 A | 10/2000 | Saadat et al. | |
| 6,139,571 A | 10/2000 | Fuller et al. | |
| 6,179,803 B1 | 1/2001 | Edwards et al. | |
| 6,208,881 B1 | 3/2001 | Champeau | |
| 6,233,490 B1 | 5/2001 | Kasevich | |
| 6,238,393 B1 | 5/2001 | Mulier et al. | |
| 6,272,370 B1 | 8/2001 | Gillies et al. | |
| 6,302,904 B1 | 10/2001 | Wallsten et al. | |
| 6,315,777 B1 | 11/2001 | Comben | |
| 6,328,735 B1 | 12/2001 | Curley et al. | |
| 6,337,994 B1 | 1/2002 | Stoianovici et al. | |
| 6,358,273 B1 | 3/2002 | Strul et al. | |
| 6,405,067 B1 | 6/2002 | Mest et al. | |
| 6,409,722 B1 | 6/2002 | Hoey et al. | |
| 6,443,947 B1 | 9/2002 | Marko et al. | |
| 6,463,332 B1 | 10/2002 | Aldrich | |
| 6,464,694 B1 | 10/2002 | Massengill | |
| 6,468,274 B1 | 10/2002 | Alleyne et al. | |
| 6,475,213 B1 | 11/2002 | Whayne et al. | |
| 6,477,396 B1 | 11/2002 | Mest et al. | |
| 6,494,902 B2 | 12/2002 | Hoey et al. | |
| 6,529,756 B1 | 3/2003 | Phan et al. | |
| 6,564,096 B2 | 5/2003 | Mest | |
| 6,565,561 B1 | 5/2003 | Goble et al. | |
| 6,603,997 B2 | 8/2003 | Doody | |
| 6,620,155 B2 | 9/2003 | Underwood et al. | |
| 6,641,580 B1 | 11/2003 | Edwards et al. | |
| 6,669,685 B1 | 12/2003 | Rizoiu et al. | |
| 6,678,552 B2 | 1/2004 | Pearlman | |
| 6,702,810 B2 | 3/2004 | McClurken et al. | |
| 6,752,802 B1 | 6/2004 | Isenberg et al. | |
| 6,772,012 B2 | 8/2004 | Ricart et al. | |
| 6,814,730 B2 | 11/2004 | Li | |
| 6,904,303 B2 | 6/2005 | Phan et al. | |
| 6,972,014 B2 | 12/2005 | Eum et al. | |
| 7,001,378 B2 | 2/2006 | Yon et al. | |
| 7,070,597 B2 | 7/2006 | Truckai et al. | |
| 7,101,369 B2 | 9/2006 | van der Welde | |
| 7,160,259 B2 | 1/2007 | Tardy et al. | |
| 7,179,256 B2 | 2/2007 | Mest | |
| 7,207,989 B2 | 4/2007 | Pike, Jr. et al. | |
| 7,244,254 B2 | 7/2007 | Brace et al. | |
| 7,270,659 B2 | 9/2007 | Ricart et al. | |
| 7,311,703 B2 | 12/2007 | Turovskiy et al. | |
| 7,387,625 B2 | 6/2008 | Hovda et al. | |
| 7,387,630 B2 | 6/2008 | Mest | |
| 7,412,273 B2 | 8/2008 | Jais et al. | |
| 7,416,552 B2 | 8/2008 | Paul et al. | |
| 7,559,905 B2 | 7/2009 | Kagosaki et al. | |
| 7,604,634 B2 | 10/2009 | Hooven | |
| 7,879,030 B2 | 2/2011 | Paul et al. | |
| 7,938,822 B1 | 5/2011 | Berzak et al. | |
| 7,951,143 B2 | 5/2011 | Wang et al. | |
| 7,993,335 B2 | 8/2011 | Rioux et al. | |
| 8,128,620 B2 | 3/2012 | Wang et al. | |
| 8,128,621 B2 | 3/2012 | Wang et al. | |
| 8,273,082 B2 | 9/2012 | Wang et al. | |
| 8,287,531 B2 | 10/2012 | Mest | |
| 8,333,762 B2 | 12/2012 | Mest et al. | |
| 8,369,922 B2 | 2/2013 | Paul et al. | |
| 8,439,907 B2 | 5/2013 | Auth et al. | |
| 8,444,638 B2 | 5/2013 | Woloszko et al. | |
| 8,449,535 B2 | 5/2013 | Deno et al. | |
| 8,515,560 B2 * | 8/2013 | Debruyne | A61K 9/0046 607/120 |
| 8,591,507 B2 | 11/2013 | Kramer et al. | |
| 8,663,226 B2 | 3/2014 | Germain | |
| 8,700,133 B2 | 4/2014 | Hann | |
| 8,702,697 B2 | 4/2014 | Curley | |
| 8,755,860 B2 | 6/2014 | Paul et al. | |
| 8,758,349 B2 | 6/2014 | Germain et al. | |
| 8,864,760 B2 | 10/2014 | Kramer et al. | |
| 8,945,121 B2 | 2/2015 | Curley | |
| 9,033,972 B2 | 5/2015 | Curley | |
| 9,125,671 B2 | 9/2015 | Germain et al. | |
| 9,138,287 B2 | 9/2015 | Curley et al. | |
| 9,138,288 B2 | 9/2015 | Curley | |
| 9,445,861 B2 | 9/2016 | Curley | |
| 9,610,396 B2 | 4/2017 | Curley et al. | |
| 2001/0031946 A1 | 10/2001 | Walker et al. | |
| 2002/0120259 A1 | 8/2002 | Lettice et al. | |
| 2002/0123749 A1 | 9/2002 | Jain | |
| 2002/0153046 A1 * | 10/2002 | Dantsker | F16K 99/0001 137/833 |
| 2002/0183735 A1 | 12/2002 | Edwards et al. | |
| 2003/0109871 A1 | 6/2003 | Johnson et al. | |
| 2003/0120271 A1 | 6/2003 | Burnside et al. | |
| 2004/0006336 A1 | 1/2004 | Swanson | |
| 2004/0116922 A1 | 6/2004 | Hovda et al. | |
| 2004/0220559 A1 | 11/2004 | Kramer et al. | |
| 2004/0230190 A1 | 11/2004 | Dahla et al. | |
| 2004/0260282 A1 | 12/2004 | Gough et al. | |
| 2005/0015081 A1 | 1/2005 | Turovskiy et al. | |
| 2005/0055019 A1 | 3/2005 | Skarda | |
| 2005/0059963 A1 | 3/2005 | Phan et al. | |
| 2005/0165391 A1 | 7/2005 | Maguire et al. | |
| 2005/0187599 A1 | 8/2005 | Sharkey et al. | |
| 2005/0192652 A1 | 9/2005 | Cioanta et al. | |
| 2005/0245923 A1 | 11/2005 | Christopherson et al. | |
| 2005/0267552 A1 | 12/2005 | Conquergood et al. | |
| 2006/0085054 A1 | 4/2006 | Zikorus et al. | |
| 2006/0118127 A1 | 6/2006 | Chinn | |
| 2006/0129091 A1 * | 6/2006 | Bonnette | A61B 17/22 604/93.01 |
| 2006/0216275 A1 | 9/2006 | Mon | |
| 2006/0259024 A1 | 11/2006 | Turovskiy et al. | |
| 2006/0276780 A1 | 12/2006 | Brace et al. | |
| 2006/0287650 A1 | 12/2006 | Cao et al. | |
| 2007/0027448 A1 | 2/2007 | Paul et al. | |
| 2007/0032786 A1 | 2/2007 | Francischelli | |
| 2007/0185483 A1 | 8/2007 | Butty et al. | |
| 2007/0219434 A1 | 9/2007 | Abreu | |
| 2007/0287998 A1 | 12/2007 | Sharareh et al. | |
| 2007/0288075 A1 | 12/2007 | Dowlatshahi | |

(56) References Cited

U.S. PATENT DOCUMENTS

| | | |
|---|---|---|
| 2008/0086073 A1 | 4/2008 | McDaniel |
| 2008/0154258 A1 | 6/2008 | Chang et al. |
| 2008/0161788 A1* | 7/2008 | Dando ............... A61B 18/1492 606/34 |
| 2008/0161797 A1 | 7/2008 | Wang et al. |
| 2008/0167650 A1 | 7/2008 | Joshi et al. |
| 2008/0275438 A1 | 11/2008 | Gadsby et al. |
| 2008/0275440 A1 | 11/2008 | Kratoska et al. |
| 2008/0288038 A1 | 11/2008 | Paul et al. |
| 2009/0069808 A1 | 3/2009 | Pike, Jr. et al. |
| 2009/0082837 A1 | 3/2009 | Gellman et al. |
| 2009/0093811 A1* | 4/2009 | Koblish ............. A61B 18/1492 606/41 |
| 2009/0118725 A1 | 5/2009 | Auth et al. |
| 2009/0118727 A1 | 5/2009 | Pearson et al. |
| 2009/0163836 A1 | 6/2009 | Sliwa |
| 2009/0192507 A1 | 7/2009 | Luttich |
| 2009/0254083 A1 | 10/2009 | Wallace et al. |
| 2010/0030098 A1 | 2/2010 | Fojtik |
| 2010/0094272 A1 | 4/2010 | Rossetto et al. |
| 2010/0198056 A1 | 8/2010 | Fabro et al. |
| 2010/0292766 A1 | 11/2010 | Duong et al. |
| 2010/0324471 A1 | 12/2010 | Flaherty et al. |
| 2011/0060349 A1 | 3/2011 | Cheng et al. |
| 2011/0137150 A1 | 6/2011 | Connor et al. |
| 2011/0160726 A1 | 6/2011 | Ingle |
| 2011/0184403 A1 | 7/2011 | Brannan |
| 2011/0190756 A1 | 8/2011 | Venkatachalam et al. |
| 2011/0230799 A1 | 9/2011 | Christian et al. |
| 2011/0251615 A1 | 10/2011 | Truckai et al. |
| 2011/0270246 A1* | 11/2011 | Clark ................. A61B 18/1492 606/41 |
| 2012/0108938 A1 | 5/2012 | Kauphusman et al. |
| 2012/0130381 A1 | 5/2012 | Germain |
| 2012/0265190 A1* | 10/2012 | Curley ................. A61B 18/082 606/28 |
| 2012/0265199 A1 | 10/2012 | Curley |
| 2012/0265200 A1 | 10/2012 | Curley |
| 2012/0265276 A1 | 10/2012 | Curley |
| 2012/0277737 A1 | 11/2012 | Curley |
| 2012/0310230 A1 | 12/2012 | Willis |
| 2014/0052117 A1 | 2/2014 | Curley |
| 2014/0058386 A1* | 2/2014 | Clark ..................... A61B 18/14 606/41 |
| 2014/0188106 A1 | 7/2014 | Curley |
| 2014/0275977 A1 | 9/2014 | Curley et al. |
| 2014/0276743 A1 | 9/2014 | Curley |
| 2014/0350542 A1 | 11/2014 | Kramer et al. |
| 2015/0066025 A1 | 3/2015 | Curley |
| 2015/0223882 A1 | 8/2015 | Curley |
| 2015/0351823 A1 | 12/2015 | Curley |
| 2015/0359582 A1 | 12/2015 | Curley et al. |
| 2016/0354138 A1 | 12/2016 | Curley |

FOREIGN PATENT DOCUMENTS

| | | |
|---|---|---|
| CN | 1897885 A | 1/2007 |
| CN | 101209217 A | 7/2008 |
| CN | 101578073 A | 11/2009 |
| CN | 201642316 U | 11/2010 |
| CN | 101999931 A | 4/2011 |
| EP | 0 895 756 A1 | 2/1999 |
| EP | 1 033 107 A1 | 9/2000 |
| EP | 0 908 156 B1 | 11/2003 |
| EP | 2 042 112 A2 | 4/2009 |
| EP | 2 430 996 A2 | 3/2012 |
| JP | 10-505268 A | 5/1998 |
| WO | 96/07360 A1 | 3/1996 |
| WO | 96/34569 A1 | 11/1996 |
| WO | 96/36288 A1 | 11/1996 |
| WO | 97/29702 A1 | 8/1997 |
| WO | 98/29068 A1 | 7/1998 |
| WO | 99/32186 A1 | 7/1999 |
| WO | 02/089686 A1 | 11/2002 |
| WO | 2005/048858 A1 | 6/2005 |
| WO | 2005/089663 A1 | 9/2005 |
| WO | 2006/055658 A1 | 5/2006 |
| WO | 2006/095171 A1 | 9/2006 |
| WO | 2006/102471 A2 | 9/2006 |
| WO | 2006/103951 A1 | 10/2006 |
| WO | 2007/080578 A2 | 7/2007 |
| WO | 2010/002733 A1 | 1/2010 |
| WO | 2010/151619 A2 | 12/2010 |
| WO | 2012/071058 A1 | 5/2012 |

OTHER PUBLICATIONS

Chinese Office Action for Application No. 201280028609.9, issued May 27, 2015. (22 pages)

Chinese Office Action for Application No. 201280028611.6, issued Jul. 29, 2015. (23 pages).

Chinese Office Action for Application No. 201280028620.5, issued May 27, 2015 (26 pages).

Chinese Office Action for Application No. 201280028621.X, issued Jul. 31, 2015. (18 pages).

Chinese Office Action for Application No. 201380053690.0, issued Sep. 30, 2016. (17 pages).

Extended Search Report and Written Opinion for EP 12770537.4 dated Oct. 10, 2014 (6 pages).

Extended Search Report and Written Opinion for EP 12770631.5 dated Oct. 1, 2014.

Extended Search Report and Written Opinion for EP 12771331.1 dated Sep. 25, 2014.

Extended European Search Report and Written Opinion for Application No. 12771601.7 issued Oct. 27, 2014 (7 pages).

Extended Search Report and Written Opinion for EP 12 77 1876 dated Oct. 13, 2014 (6 pages).

Extended European Search Report and Search Opinion for Application No. 13829821.1 issued Mar. 17, 2016 (7 pages).

International Search Report and Written Opinion for Application No. PCT/US2012/033203, issued Sep. 21, 2012. (23 pages).

International Search Report and Written Opinion for Application No. PCT/US2012/033213, issued Sep. 21, 2012. (17 pages).

International Search Report and Written Opinion for Application No. PCT/US2012/033216, issued Sep. 21, 2012. (17 pages).

International Search Report and Written Opinion for Application No. PCT/US2012/033327, issued Sep. 21, 2012. (14 pages).

International Search Report and Written Opinion for Application No. PCT/US2012/033332, issued Sep. 21, 2012. (20 pages).

International Search Report and Written Opinion for Application No. PCT/US2013/053977, issued Nov. 14, 2013. (20 pages).

International Search Report and Written Opinion for Application No. PCT/US2014/024731, mailed Jul. 21, 2014 (39 pages).

Japanese Office Action for Application No. 2014-505263, mailed Jan. 26, 2016 (4 pages).

Japanese Office Action for Application No. 2014-505266, mailed Feb. 23, 2016 (7 pages).

David R. Lide (ed)., CRC Handbook of Chemistry and Physics, 87th Edition. 2006. p. 8-81. CRC Press, Florida.

Nath et al., Prog. Card. Dis. 37(4):185-204 (1995).

Rolf Sander, Compilation of Henry's Law Constants for Inorganic and Organic Species of Potential Importance in Environmental Chemistry. Max-Planck Institute of Chemistry. 1999, Mainz Germany. www.henrys-law.org.

Sapareto et al., Int. J Rad. One. Biol. Phys. 10(6):787-800 (1984).

Young, S.T., et al., An instrument using variation of resistance to aid in needle tip insertion in epidural block in monkeys. Med Instrum. Oct. 1987;21(5):266-8. Abstract Only.

* cited by examiner

A-A

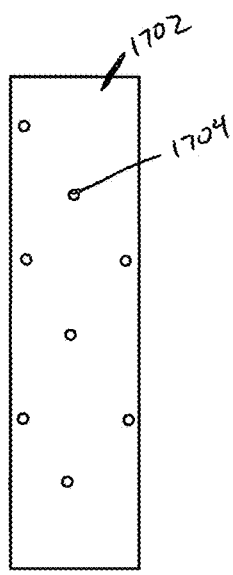 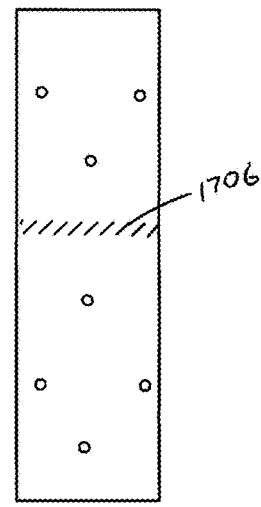
FIG. 15A　　　　FIG. 15B
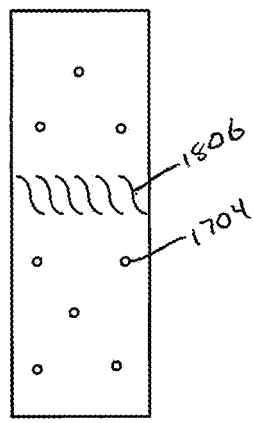 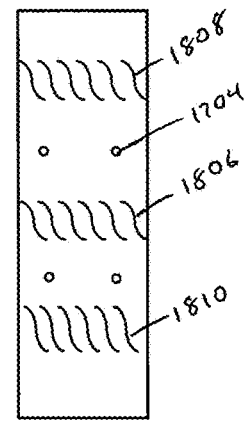 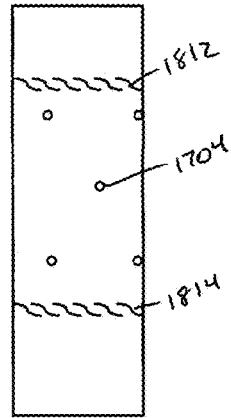
FIG. 16A　　　FIG. 16B　　　FIG. 16C

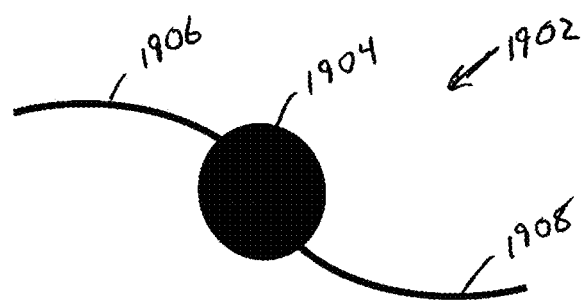
FIG. 17
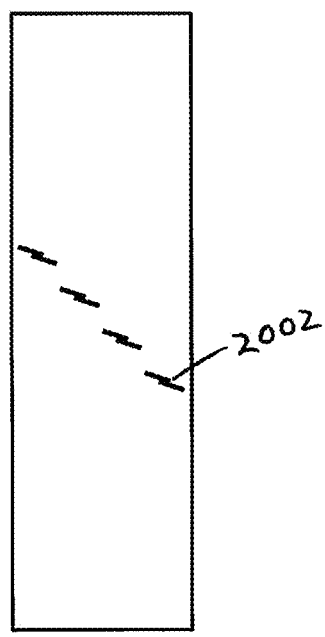 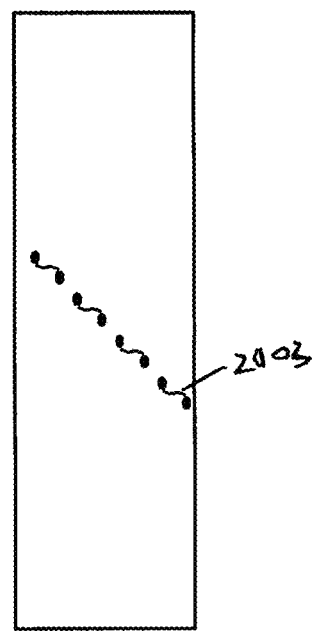
FIG. 18A                FIG. 18B

DEVICES AND METHODS FOR DELIVERING FLUID TO TISSUE DURING ABLATION THERAPY

FIELD

This disclosure relates generally to surgical instruments and, more particularly, to such instruments that deliver fluid to tissue in connection with ablation therapy.

BACKGROUND

Fluid enhanced ablation therapy involves the introduction of a fluid into a volume of tissue to deliver a therapeutic dose of energy in order to destroy tissue. The fluid can act as a therapeutic agent delivering thermal energy into the tissue volume—thermal energy supplied from the fluid itself (e.g., a heated fluid) or from an ablation element that provides thermal energy using, e.g., radio frequency (RF) electrical energy, microwave or light wave electromagnetic energy, ultrasonic vibrational energy, etc. This therapy can be applied to a variety of procedures, including the destruction of tumors.

One example of fluid enhanced ablation therapy is the ablation technique described in U.S. Pat. No. 6,328,735, which is hereby incorporated by reference in its entirety. Using the ablation technique described therein, saline is passed through a needle and heated, and the heated fluid is delivered into a target volume of tissue surrounding the needle. In addition, RF electrical current is simultaneously passed through the tissue between an emitter electrode positioned on the needle and a remotely located return electrode. The saline acts as a therapeutic agent to transport thermal energy to the target volume of tissue via convection, and the RF electrical energy can act to supplement and/or replenish the thermal energy of the fluid that is lost as it moves through the tissue. The delivery of thermal energy via the movement of fluid through tissue can allow a greater volume of tissue to be treated with a therapeutic dose of ablative energy than is possible with other known techniques. The therapy is usually completed once the target volume of tissue reaches a desired therapeutic temperature, or otherwise receives a therapeutic dose of energy.

Fluid enhanced ablation therapy can have a number of advantages over, e.g., conventional RF ablation techniques. For example, the delivery of fluid in combination with RF energy can more effectively convect the heat developed near the RF electrode into the surrounding tissue. This can prevent tissue adjacent to the RF electrode from charring and desiccating due to the accumulation of too much thermal energy near the electrode. In conventional RF ablation, this charring can occur in tissue near the electrode even after only a short amount of time. Tissue charring can be problematic because it is accompanied by an increase in tissue impedance that can prevent the transmission of RF energy through the tissue, thereby effectively ending the therapy. Localized overheating of tissue can also cause so-called "steam pops," which are explosive phase changes of liquid contained in tissue. If the fluid has a higher conductivity than the surrounding tissue, the volume rate of deposition of RF energy immediately adjacent to the RF electrode can be reduced somewhat, further decreasing the risks of charring and desiccation adjacent to the RF electrode.

As a result, it is desirable that fluid be delivered into tissue wherever RF or other ablative energy is being delivered. References such as U.S. Pat. No. 6,328,735 contemplate delivering fluid throughout an RF energy field, however, it has been discovered that the devices described therein do not actually produce the desired uniform fluid distribution field. Rather, as explained in more detail below and illustrated in FIG. 3, fluid is delivered only from a distal end portion of the device. Moreover, in other devices fluid is intentionally delivered only from a distal-most end of the device via, for example, a single opening at a distal end of the device or a plurality of openings positioned at or adjacent to a distal end of the device. In such devices, an electrode or other energy delivery element often extends proximally from the one or more openings and there can be a misalignment between the RF or other energy field and the fluid distribution field. Regardless of the particular configuration of a device, a lack of fluid delivery along an entire length of, for example, an ablation electrode or other portion of a device intended to deliver thermal energy and fluid can reduce the effectiveness of the therapy and lead to potential complications for a patient.

Accordingly, there is a need for improved devices and methods for delivering fluid to tissue during ablation therapy. More particularly, there is a need for new devices and methods for ensuring that fluid is delivered in a desired distribution from a plurality of outlet ports during an ablation procedure, such as fluid enhanced ablation therapy.

SUMMARY

The present disclosure generally provides devices and methods for delivering fluid to tissue during ablation therapy, including, for example, during fluid enhanced ablation therapy procedures. The devices and methods described herein generally provide a more uniform distribution—or a desired non-uniform distribution—of fluid flow from a plurality of outlet ports formed in, for example, an elongate body of an ablation device. Because the plurality of outlet ports are positioned to create a desired fluid flow pattern in tissue, where such a pattern optimizes the performance of the ablation therapy, providing uniform or desired flow from each of the outlet ports can ensure the therapy proceeds as intended and is as efficient as possible.

The devices and methods described herein generally achieve improved fluid distribution and delivery by, counterintuitively, adding flow resistance to the device. Adding or otherwise adjusting flow resistance can include adjusting either or both of resistance to fluid flow per unit length of lumen and resistance to fluid flow from an elongate body lumen into tissue surrounding the elongate body. For example, the devices and methods described herein can include increasing levels of flow resistance to fluid flow from a plurality of outlet ports. Moreover, such resistance can vary from a proximal to a distal end of a portion of an elongate body or other device that includes such outlet ports. For example, such resistance can increase from the proximal to the distal end of the portion of the elongate body or other device that includes the outlet ports. In other embodiments, a resistance per unit length of lumen/elongate body to fluid flow through the lumen/elongate body can similarly be increased, and can increase along a length of the elongate body from a proximal to a distal end thereof. While counter to typical intuition that reduced flow resistance via, e.g., increased outlet port numbers, sizes, etc. would allow for increased flow, the addition of flow resistance can ensure there is sufficient fluid pressure near each outlet port to cause fluid to flow therefrom.

Increasing flow resistance along a length of an elongate body or other ablation device can be accomplished in a number of manners. In some embodiments, for example, the number, size, shape, orientation, and positioning of the plurality of outlet ports can be adjusted to provide better flow from all or a subset of the outlet ports. This can mean, for example, decreasing a size of outlet ports formed more distally along an elongate body or other ablation device, while increasing or maintaining a size of outlet ports formed more proximally. In addition, relative spacing between adjacent outlet ports, or pitch of a series of outlet ports arranged around an elongate body, can be adjusted to provide fewer outlet ports along a distal portion of an elongate body and more outlet ports along a proximal portion thereof.

In some embodiments, the number, size, and shape of the plurality of outlet ports can be adjusted to maintain a ratio of the cumulative or combined area of the outlet ports (i.e., a sum of the cross-sectional areas of each of the plurality of outlet ports) to the area of the inner lumen (i.e., the cross-sectional area through which fluid can flow, sometimes referred to herein as inner lumen cross-sectional flow area) at or below a certain level. For example, it can be desirable to maintain this ratio below a level of about 3:1 to maintain desired fluid flow from all outlet ports.

In still other embodiments, the cross-sectional area of an inner lumen delivering fluid to the outlet ports can be reduced from a proximal to a distal end thereof to increase flow resistance therewithin. For example, a tapered flow diverter or other structure can be disposed within an inner lumen of an elongate body or other device in the vicinity of the outlet ports. Alternatively, a diameter of the inner lumen can decrease from a proximal portion of an elongate body or other device to a distal portion thereof via, for example, tapered sidewalls of varying thickness. Accordingly, the area of the inner lumen at a particular point, or the volume of a selected portion of the inner lumen, can reduce as one moves distally along a device.

By utilizing the above-mentioned techniques and structures, ablation devices can be constructed that provide improved distribution of fluid from a plurality of outlet ports. For example, an ablation device can be constructed wherein no more than about 70% by volume of fluid delivered to tissue is emitted from the distal-most 25% of outlet ports on the device. In other embodiments, no more than about 70% by volume of the fluid delivered to tissue is emitted from the proximal-most 25% of outlet ports. In other embodiments, any desired fluid flow distribution can be created, for example, a distribution in which no more than 33% by volume of fluid delivered to tissue is emitted from a distal-most 25% of outlet ports on the device. Using the techniques described herein, fluid distribution patterns can be selected so as to produce any desired percentage of fluid flow by volume from any desired group of outlet ports, e.g., no more than 50% by volume of fluid delivered from a distal-most 30% of outlet ports, etc. Importantly, however, the almost complete distal-port flow bias observed in prior art devices can be avoided by producing a significant amount of fluid flow from one or more outlet ports disposed along a proximal portion of fluid delivery region of a device.

In one aspect, an ablation device is provided that can include an elongate body having an inner lumen and a plurality of outlet ports formed in the elongate body that are disposed along a length thereof. The plurality of outlet ports can be configured to deliver fluid from the inner lumen to tissue surrounding the elongate body. The device can further include an ablation element configured to heat the tissue surrounding the elongate body. Further, a flow resistance of the elongate body can increase along the length of the elongate body containing the plurality of outlet ports from a proximal end thereof to a distal end thereof.

The flow resistance of the elongate body can include any of a flow resistance per unit length of lumen and a resistance to fluid flow from the lumen through any outlet ports into, for example, tissue surrounding the elongate body. Adjusting either or both of these parameters can effect a change in flow resistance of the elongate body.

The devices and methods described herein can include a variety of additional features or modifications, all of which are considered within the scope of the present disclosure. For example, in some embodiments a ratio of a sum of an area of each of the plurality of outlet ports to an area of the inner lumen can be less than about 3:1.

In other embodiments, a flow resistance to fluid flow through a distal 25% of the plurality of outlet ports can be such that they deliver less than about 70% by volume of fluid delivered into tissue from the plurality of outlet ports. In other embodiments, a flow resistance to fluid flow through a distal 25% of the plurality of outlet ports can be such that they deliver less than about 55% by volume of fluid delivered into tissue from the plurality of outlet ports. In still other embodiments, a flow resistance to fluid flow through a distal 25% of the plurality of outlet ports can be such that they deliver less than about 40% by volume of fluid delivered into tissue from the plurality of outlet ports. In yet other embodiments, a flow resistance to fluid flow through a distal 25% of the plurality of outlet ports can be such that they deliver less than about 25% by volume of fluid delivered into tissue from the plurality of outlet ports.

In some embodiments, a flow resistance to fluid flow through a central 50% of the plurality of outlet ports can be such that they deliver more than about 25% by volume of fluid delivered into tissue from the plurality of outlet ports. In other embodiments, a flow resistance to fluid flow through a central 50% of the plurality of outlet ports can be such that they deliver more than about 35% by volume of fluid delivered into tissue from the plurality of outlet ports. In still other embodiments, a flow resistance to fluid flow through a central 50% of the plurality of outlet ports can be such that they deliver more than about 45% by volume of fluid delivered into tissue from the plurality of outlet ports. In yet other embodiments, a flow resistance to fluid flow through a central 50% of the plurality of outlet ports can be such that they deliver more than about 55% by volume of fluid delivered into tissue from the plurality of outlet ports.

In still other embodiments, a cross-sectional area of each of the plurality of outlet ports can decrease from a proximal end of the elongate body to a distal end of the elongate body. For example, in embodiments utilizing a plurality of circular outlet ports, a diameter of the outlet ports can decrease from a proximal end of the elongate body to a distal end thereof. In certain embodiments, spacing between adjacent axially-aligned outlet ports (e.g., adjacent outlet ports aligned with one another along an axis parallel to a longitudinal axis of the elongate body) can increase from a proximal end of the elongate body to a distal end of the elongate body in place of variation of diameter. Variations in diameter and spacing can be combined with one another in some embodiments, however.

In certain embodiments, at least one of the plurality of outlet ports can have a non-circular shape. For example, at least one of the plurality of outlet ports can have a slot shape. Any number of other shapes are also possible, including hybrids of slots (e.g., tapered slots, etc.), circles, and other shapes.

In some embodiments, a cross-sectional area of the inner lumen through which fluid can flow (sometimes referred to herein as "cross-sectional flow area") can decrease along at least a portion of a length of the elongate body containing the plurality of outlet ports. This reduction in cross-sectional flow area as fluid moves distally can add flow resistance per unit length of lumen to fluid flow and stall fluid flow farther back toward a proximal end of the elongate body, thereby creating more uniform flow from the plurality of outlet ports. Reducing cross-sectional flow area can be accomplished in a variety of manners. For example, in some embodiments a diameter of the inner lumen can decrease along the length of the elongate body containing the plurality of outlet ports from a proximal end thereof to a distal end thereof. By way of further example, tapered elongate body sidewalls of varying thickness can be used to create such a narrowing of the diameter of the inner lumen from a proximal to a distal end thereof.

In some embodiments, the device can further include a flow diverter disposed within the inner lumen of the elongate body along the length of the elongate body containing the plurality of outlet ports. The flow diverter can serve to reduce the cross-sectional area of the inner lumen and thereby increase flow resistance per unit length of lumen to fluid flow. The flow diverter can, for example, increase in diameter from a proximal end thereof to a distal end thereof. Of course, in some embodiments a flow diverter can be combined with, for example, tapered elongate body sidewalls of varying thickness to further reduce cross-sectional flow area over at least a portion of the length of the elongate body.

As noted above, the ablation element can be any of a variety of ablation elements known in the art and configured to deliver ablative energy to surrounding tissue. In some embodiments, the ablation element can be a radio frequency electrode disposed along a length of the elongate body, such as a ring of conductive material disposed over a non-conductive elongate body or a portion of a conductive elongate body that is left uncovered by an electrically insulating material. The device can further include at least one outlet port positioned at least partially beyond a boundary of the ablation element to deliver fluid to tissue immediately adjacent to the boundary of the ablation element. In some embodiments, one or more outlet ports can be positioned across or adjacent to a boundary of the ablation element. Placing outlet ports on or near an electrode or other ablation element boundary, including at locations at least partially beyond the boundary, can serve to counteract increased current density, and attendant heating, that can occur in areas adjacent to ablation element boundaries.

In another aspect, an ablation device is provided that includes an elongate body having an inner lumen, the elongate body including a fluid delivery portion extending along a length thereof that includes a plurality of outlet ports configured to deliver fluid from the inner lumen to tissue surrounding the elongate body. The device can further include an ablation element configured to heat tissue surrounding the elongate body. Moreover, the fluid delivery portion of the elongate body can be configured such that less than about 70% by volume of fluid delivered to tissue is emitted from outlet ports disposed in a distal 25% of the fluid delivery portion.

In some embodiments, the fluid delivery portion can be further configured such that less than about 55% by volume of fluid delivered to tissue is emitted from outlet ports disposed in a distal 25% of the fluid delivery portion. In other embodiments, the fluid delivery portion can be further configured such that less than about 70% by volume of fluid delivered to tissue is emitted from outlet ports disposed in a proximal 25% of the fluid delivery portion. In still other embodiments, the fluid delivery portion can be further configured such that less than about 55% by volume of fluid delivered to tissue is emitted from outlet ports disposed in a proximal 25% of the fluid delivery portion. In yet other embodiments, the fluid delivery portion can be further configured such that no more than about 70% by volume of fluid delivered to tissue is emitted from outlet ports disposed in a central 50% of the fluid delivery portion.

Other combinations and fluid flow distributions are also possible and considered within the scope of the present disclosure. For example, any desired predetermined fluid distribution pattern is possible, with any desired percentage of fluid by volume being delivered from any desired subset of outlet ports formed in the elongate body. For example, the fluid delivery portion can be configured such that less than a predetermined percentage by volume of fluid delivered to tissue is emitted from outlet ports disposed in a predetermined portion of the elongate body or outlet ports formed therein. The predetermined percentage can be, for example, 25%, 35%, 50%, 70%, or other values in certain embodiments, and the predetermined portion of the elongate body or outlet ports can be a distal 25%, 30%, 35%, etc., a proximal 25%, 30%, 35%, etc., a central 50%, 60%, 70%, etc. It can be desirable in some embodiments to avoid a strong flow bias in any one portion of the elongate body configured to deliver fluid to tissue, e.g., a proximal portion, distal portion, or central portion.

In still another aspect, an ablation device is provided that includes a catheter-delivered elongate body having an inner lumen and a plurality of outlet ports formed in the elongate body, each of the plurality of outlet ports defining an area configured to pass fluid from the inner lumen to tissue surrounding the elongate body. The device can further include an ablation element configured to heat the tissue surrounding the elongate body. Further, a ratio of a sum of the areas of each of the plurality of outlet ports to an area of the inner lumen can be less than about 3:1.

In some embodiments, the ratio of the sum of the areas of each of the plurality of outlet ports to the area of the inner lumen can be less than about 2.5:1. In other embodiments, the ratio of the sum of the areas of each of the plurality of outlet ports to the area of the inner lumen can be less than about 2:1. More particularly, in some embodiments the ratio of the sum of the areas of each of the plurality of outlet ports to the area of the inner lumen can be less than about 1.3:1. In still other embodiments, the ratio of the sum of the areas of each of the plurality of outlet ports to the area of the inner lumen can be between about 0.5:1 and about 2:1, or the equivalent of 1×/÷2 (1 times or divide by 2).

In certain embodiments, a cross-sectional area of the inner lumen through which fluid can flow can decrease from a proximal end to a distal end of a length of the elongate body that includes the plurality of outlet ports. In some embodiments, this can be accomplished via a diameter of the inner lumen that decreases from the proximal end to the distal end of the length of the elongate body that includes the plurality of outlet ports. In other embodiments, this can be accomplished via a flow diverter disposed within the inner lumen of the elongate body along the length of the elongate body that includes the plurality of outlet ports. A diameter of the flow diverter can increase from a proximal end thereof to a distal end thereof, thereby progressively reducing the cross-sectional area of the inner lumen available for fluid flow. In some embodiments, varying a cross-sectional flow area of the inner lumen (using, for example, a varying inner lumen diameter, a flow diverter, or a combination thereof) can be combined with selection of outlet port size to achieve the various ratios mentioned above and further enhance the flow resistance to flow within the inner lumen that can produce uniform fluid delivery from all of the outlet ports.

In another aspect, an ablation device is provided that includes an elongate body having an inner lumen and including a fluid delivery portion extending along a length thereof. The fluid delivery portion can have a plurality of outlet ports configured to deliver fluid from the inner lumen to tissue surrounding the elongate body. The device can further include an ablation element configured to heat tissue surrounding the elongate body. Moreover, a cross-sectional area of the inner lumen through which fluid can flow can decrease from a proximal end of the fluid delivery portion of the elongate body to a distal end thereof.

In certain embodiments, a diameter of the inner lumen can decrease from a proximal end to a distal end of the fluid delivery portion of the elongate body. In other embodiments, the device can further include a flow diverter disposed within the fluid delivery portion of the inner lumen of the elongate body. The flow diverter can, in some embodiments, have a substantially conical shape that increases in diameter from a proximal end thereof to a distal end thereof.

In certain embodiments, any of a number of surface features or other variations can be incorporated into the flow diverter to create localized changes in fluid flow. For example, in some embodiments the flow diverter can include any of at least one step to transition from a first diameter to a second diameter and at least one recess. A step (or steps) can create a localized change in fluid flow by further restricting the cross-sectional area through which fluid can flow and by introducing an abrupt change in direction to fluid flow. Conversely, a recess formed in the flow diverter can create a localized change in fluid flow by increasing the cross-sectional area through which fluid can flow and reducing the fluid pressure experienced near the recess. A step (or steps) or recess (or recesses) can be positioned anywhere along the flow diverter but, in some embodiments, can be aligned with one of the plurality of outlet ports formed in the elongate body. Positioning a step, recess, or other feature of the flow diverter in alignment with one of the plurality of outlet ports can create localized changes in flow (e.g., an increase or decrease) from that particular outlet port.

In some embodiments, the device can further include a thermocouple positioned at a proximal end of the flow diverter. In still other embodiments, the device can further include a heating element positioned at a proximal end of the flow diverter and configured to heat fluid flowing within the inner lumen.

In certain embodiments, the inner lumen through which the fluid can flow can also include a fluid heater that heats the fluid as it flows through the fluid delivery system.

Any of the features or variations described above can be applied to any particular aspect or embodiment of the present disclosure in a number of different combinations. The absence of explicit recitation of any particular combination is due solely to the avoidance of repetition in this summary.

BRIEF DESCRIPTION OF THE DRAWINGS

The aspects and embodiments described above will be more fully understood from the following detailed description taken in conjunction with the accompanying drawings, in which:

FIG. 15A is a side view of one embodiment of an outlet port pattern of an elongate body;

FIG. 15B is a side view of an alternative embodiment of an outlet port pattern of an elongate body;

FIG. 16A is a side view of one embodiment of an outlet port pattern of an elongate body;

FIG. 16B is a side view of an alternative embodiment of an outlet port pattern of an elongate body;

FIG. 16C is a side view of another embodiment of an outlet port pattern of an elongate body;

FIG. 17 is a diagram of one embodiment of a non-circular outlet port shape;

FIG. 18A is a side view of one embodiment of an outlet port pattern of an elongate body;

FIG. 18B is a side view of an alternative embodiment of an outlet port pattern of an elongate body;

DETAILED DESCRIPTION

Figure 1:
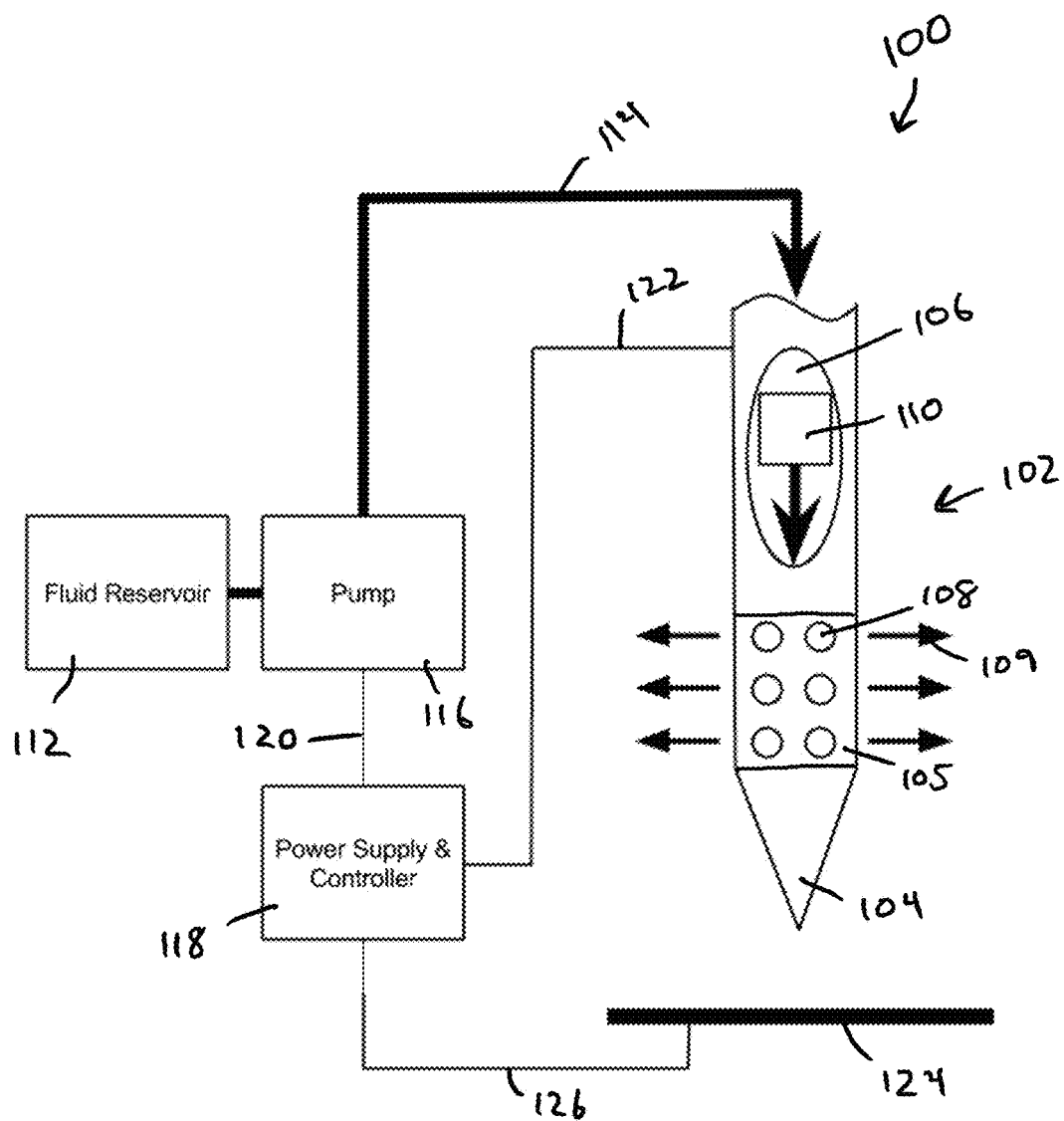
FIG. 1 is a diagram of one embodiment of a fluid enhanced ablation therapy system.

Certain exemplary embodiments will now be described to provide an overall understanding of the principles of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

To the extent that linear or circular dimensions are used in the description of the disclosed devices and methods, such dimensions are not intended to limit the types of shapes that can be used in conjunction with such devices and methods. Equivalents to such linear and circular dimensions can easily be determined for any geometric shape. Further, in the present disclosure, like-numbered components of the embodiments generally have similar features. Still further, sizes and shapes of the devices, and the components thereof, can depend at least on the anatomy of the subject in which the devices will be used, the size and shape of components with which the devices will be used, and the methods and procedures in which the devices will be used.

Fluid enhanced ablation therapy, as mentioned above, is defined by passing a fluid into tissue to act as a therapeutic agent and deliver thermal energy into the tissue. The thermal energy can be provided from the fluid itself (e.g., by using heated fluid), by delivering therapeutic energy from an ablation element (e.g., an RF electrode), or a combination of the two. The delivery of therapeutic energy into tissue can cause hyperthermia in the tissue, ultimately resulting in necrosis. This temperature-induced selective destruction of tissue can be utilized to treat a variety of conditions including tumors, fibroids, cardiac dysrhythmias (e.g., ventricular tachycardia, etc.), and others.

The ablation technique described in U.S. Pat. No. 6,328,735 and incorporated by reference above delivers fluid heated to a therapeutic temperature into tissue along with ablative energy. The heated fluid acts as a therapeutic agent by flowing through the extracellular space of the treatment tissue and increasing the heat transfer through the tissue significantly. In particular, the flowing heated fluid convects thermal energy into the target tissue. The thermal energy can be supplied from the heated fluid itself and the ablation energy source can act to replenish thermal energy lost from the fluid as it moves through the tissue. Furthermore, the fluid can serve to constantly hydrate the tissue and prevent any tissue charring and associated impedance rise near the ablation element, as described in more detail below. Still further, the fluid can regulate the temperature of the tissue and prevent localized overheating that can cause, for example, so-called "steam pops," which are the explosive phase change of liquid in the tissue.

Fluid enhanced ablation therapy can have a number of advantages over prior art ablation techniques, such as conventional RF ablation. For example, conventional RF ablation often overheats the tissue located adjacent to the emitter electrode because the heat cannot be efficiently transported away from the electrode. This overheating can cause charring of the tissue and an associated rise in impedance that can effectively terminate the therapy. During fluid enhanced ablation therapy, the therapeutically heated fluid can convect heat deeper into the target tissue, thereby reducing tissue charring and the associated impedance change of the tissue. Further, because the fluid is heated to a therapeutic level, it does not act as a heat sink that draws down the temperature of the surrounding tissue. Instead, the fluid itself acts as the therapeutic agent delivering thermal energy into the tissue and the RF energy can act to counter the loss of thermal energy from the fluid as it moves through the tissue. Therefore, the concurrent application of RF energy and injection of heated fluid into the tissue can eliminate the desiccation and/or vaporization of tissue adjacent to the electrode, maintain the effective tissue impedance, and increase the thermal transport within the tissue being heated with RF energy. The total volume of tissue that can be heated to therapeutic temperatures is thereby increased when compared to conventional RF ablation.

In addition, fluid enhanced ablation therapy devices have a greater number of parameters that can be varied to adjust the shape of the treated volume of tissue. For example, an operator or control system can modify parameters such as fluid temperature (e.g., from about 40° C. to about 100° C.), fluid flow rate (e.g., from about 0 ml/min to about 50 ml/min), RF power (e.g., from about 0 W to about 200 W), and duration of treatment (e.g., from about 0 min to about 10 min) to adjust the temperature profile within the target volume of tissue. The composition, ionic content, and dissolved oxygen content of the delivered fluid can also be varied to improve effectiveness of thermal energy delivery within the target tissue. Still further, different electrode configurations can be used to vary the treatment. For example, an emitter electrode can be configured as a continuous cylindrical band around a needle or other elongate body, or the electrode can be formed in other geometries, such as spherical or helical. The electrode can form a continuous surface area, or it can have a plurality of discrete portions. Moreover, electrodes in monopolar or bipolar configurations can be utilized. Further examples of how a treated volume of tissue can be selectively shaped by varying the parameters of fluid enhanced ablation therapy can be found in U.S. Pat. No. 8,702,697, entitled "Devices and Methods for Shaping Therapy in Fluid Enhanced Ablation," which is hereby incorporated by reference in its entirety.

FIG. 1 illustrates a diagram of one embodiment of a fluid enhanced ablation system 100. The system includes an elongate body 102 configured for insertion into a target volume of tissue. The elongate body can have a variety of shapes and sizes according to the geometry of the target tissue. Further, the particular size of the elongate body can depend on a variety of factors including the type and location of tissue to be treated, the size of the tissue volume to be treated, etc. By way of example only, in one embodiment, the elongate body can be a thin-walled stainless steel needle between about 16- and about 18-gauge (i.e., an outer diameter of about 1.27 mm to about 1.65 mm), and having a length that is approximately 25 cm. The elongate body 102 can include a pointed distal tip 104 configured to puncture tissue to facilitate introduction of the device into a target volume of tissue, however, in other embodiments the tip can be blunt and can have various other configurations. The elongate body 102 can be formed from a conductive material such that the elongate body can conduct electrical energy along its length to one or more ablation elements located along a distal portion of the elongate body. Emitter electrode 105 is an example of an ablation element capable of delivering RF energy from the elongate body.

In some embodiments, the emitter electrode 105 can be a portion of the elongate body 102. For example, the elongate body 102 can be coated in an insulating material along its entire length except for the portion representing the emitter electrode 105. More particularly, in one embodiment, the elongate body 102 can be coated with 1.5 mil of the fluoropolymer Xylan™ 8840. In other embodiments, different coatings can be used in place of, or in conjunction with, the fluoropolymer coating. For example, in certain embodiments, 1 mil of Polyester shrink tubing can be disposed over the Xylan coating. The electrode 105 can have a variety of lengths and shape configurations. In one embodiment, the electrode 105 can be a 4 mm section of a tubular elongate body that is exposed to surrounding tissue. Further, the electrode 105 can be located anywhere along the length of the elongate body 105 (and there can also be more than one electrode disposed along the length of the elongate body). In one embodiment, the electrode can be located adjacent to the distal tip 104. In other embodiments, the elongate body can be formed from an insulating material, and the electrode can be disposed around the elongate body or between portions of the elongate body, e.g., as a conductive metal ring surrounding a polymer elongate body, etc.

The electrode can be formed from a variety of materials suitable for conducting current. Any metal or metal salt may be used. Aside from stainless steel, exemplary metals include platinum, gold, or silver, and exemplary metal salts include silver/silver chloride. In one embodiment, the electrode can be formed from silver/silver chloride. It is known that metal electrodes assume a voltage potential different from that of surrounding tissue and/or liquid. Passing a current through this voltage difference can result in energy dissipation at the electrode/tissue interface, which can exacerbate excessive heating of the tissue near the electrodes. One advantage of using a metal salt such as silver/silver chloride is that it has a high exchange current density. As a result, a large amount of current can be passed through such an electrode into tissue with only a small voltage drop, thereby minimizing energy dissipation at this interface. Thus, an electrode formed from a metal salt such as silver/silver chloride can reduce excessive energy generation at the tissue interface and thereby produce a more desirable therapeutic temperature profile, even where there is no liquid flow about the electrode.

As mentioned above, the ablation element included in a fluid enhanced ablation therapy device can be configured to deliver a variety of types of energy into tissue surrounding the device. An ablation element, such as the electrode 105, that is configured to deliver RF electrical energy is just one example of an ablation element that can be utilized with the methods and devices described herein. For example, an alternative ablation element configured to deliver microwave electromagnetic energy is described in U.S. Pat. No. 9,033,972, entitled "Methods and Devices for Fluid Enhanced Microwave Ablation Therapy," which is hereby incorporated by reference in its entirety. Other exemplary ablation elements can be configured to deliver, for example, any type of electrical energy, electromagnetic energy, or ultrasonic vibrational energy.

The electrode 105 or other ablation element, or other portion of the elongate body 102, can include one or more outlet ports 108 that are configured to deliver fluid from an inner lumen 106 extending through the elongate body into surrounding tissue (as shown by arrows 109). The outlet ports 108 can be formed in a variety of sizes, numbers, and pattern configurations. In addition, the outlet ports 108 can be configured to direct fluid in a variety of directions with respect to the elongate body 102. These can include the normal orientation (i.e., perpendicular to the elongate body surface) shown by arrows 109, as well as orientations directed proximally and distally along a longitudinal axis of the elongate body 102, including various orientations that develop a circular or spiral flow of liquid around the elongate body. Still further, in some embodiments, the elongate body 102 can be formed with an open distal end that serves as an outlet port. Further details of the outlet ports 108 are discussed below.

The inner lumen 106 that communicates with the outlet ports 108 can also house a heating assembly 110 configured to heat fluid as it passes through the inner lumen 106 just prior to being introduced into tissue. The heating assembly 110 can have a variety of configurations and, in one embodiment, can include two wires suspended within the inner lumen 106. The wires can be configured to pass RF energy therebetween in order to heat fluid flowing through the inner lumen 106. In other embodiments, a single wire can be configured to pass RF energy between the wire and the inner walls of the elongate body. Further description of exemplary heating assemblies can be found in U.S. Pat. Pub. No. 2012/0265190, entitled "Methods and Devices for Heating Fluid in Fluid Enhanced Ablation Therapy," which is hereby incorporated by reference in its entirety.

The portion of the elongate body located distal to the electrode 105 or other ablation element can be solid or filled such that the inner lumen 106 terminates at the distal end of the electrode 105. In one embodiment, the inner volume of the portion of the elongate body distal to the electrode can be filled with a plastic plug that can be epoxied in place or held by an interference fit. In other embodiments, the portion of the elongate body distal to the electrode can be formed from solid metal and attached to the proximal portion of the elongate body by welding, swaging, or any other technique known in the art. As noted above, in some embodiments the elongate body can include one or more outlet ports formed at or near a distal end thereof. Such outlet ports can be formed through a plastic plug or other element described above that may be disposed near a distal end of the elongate body, or an opening can be provided in place of such an element.

The elongate body 102 illustrated in FIG. 1 can be configured for insertion into a patient's body in a variety of manners. For example, the elongate body 102 can be incorporated into a device intended for laparoscopic or percutaneous insertion into a patient's body, for example when treating cancerous tissue in a patient's liver. In addition to the elongate body 102, a device can include a handle to allow an operator to manipulate the device and the handle can include one or more electrical connections that connect various components of the elongate body (e.g., the heating assembly and ablation element 205) to, for example, the controller 118 shown in FIG. 1. The handle can also include at least one fluid conduit for connecting a fluid source to the device.

Such a device is just one exemplary embodiment of a medical device that can be adapted for use in fluid enhanced ablation therapy, however. In other embodiments, for example, a very small elongate body can be required when treating cardiac dysrhythmias, such as ventricular tachycardia. In such a case, an appropriately sized needle or other elongate body can be, for example, disposed at a distal end of a catheter configured for insertion into the heart via the circulatory system. In one embodiment, a stainless steel needle body between about 20- and about 30-gauge (i.e., an outer diameter of about 0.3 mm to about 0.9 mm) can be disposed at a distal end of a catheter. The catheter can have a variety of sizes but, in some embodiments, it can have a length of about 120 cm and a diameter of about 8 French ("French" is a unit of measure used in the catheter industry to describe the size of a catheter and is equal to three times the diameter of the catheter in millimeters). Other variations can include, for example, a low profile form factor for use in space-constrained environments and the inclusion of additional components, such as one or more temperature sensors to monitor the temperature of tissue in the treatment volume. Further details on these exemplary features can be found in U.S. Pat. Pub. No. 2014/0052117, entitled "Low Profile Fluid Enhanced Ablation Therapy Devices and Methods," as well as U.S. Pat. Pub. No. 2012/0277737, entitled "Devices and Methods for Remote Temperature Monitoring in Fluid Enhanced Ablation Therapy." Each of these applications is hereby incorporated by reference in their entirety.

Referring back to FIG. 1, an exemplary fluid source is shown as a fluid reservoir 112. The fluid reservoir 112 can have a variety of geometries and sizes. In one embodiment, the fluid reservoir 112 can be a cylindrical container similar to a syringe barrel that can be used with a linear pump, as described below. The fluid reservoir 112 can be connected to the inner lumen 106 via a fluid conduit 114 to supply fluid to the inner lumen and heating assembly 110. The fluid conduit 114 can be, for example, a length of flexible plastic tubing. The fluid conduit 114 can also be a rigid tube, or a combination of rigid and flexible tubing. A fluid used in the fluid reservoir 112 can be selected to provide the desired therapeutic and physical properties when applied to the target tissue, and a sterile fluid is recommended to guard against infection of the tissue. A preferred fluid for use in fluid-enhanced RF ablation is sterile normal saline solution (defined as a salt-containing solution). In some embodiments, the fluid can be modified to enhance the effectiveness of the therapy. For example, in some embodiments dissolved gasses can be removed from the fluid prior to use, a contrast agent can be added to the fluid to make it imageable using a medical imaging technology, or the ionic content of the fluid can otherwise be modified to enhance conductivity of the surrounding tissue. Further details on these exemplary features can be found in U.S. Pat. No. 8,945,121, entitled "Methods and Devices for Use of Degassed Fluids with Fluid Enhanced Ablation Devices," as well as U.S. Pat. Pub. No. 2014/0275977, entitled "Systems and Methods for Visualizing Fluid Enhanced Ablation Therapy." Each of these applications is hereby incorporated by reference in their entirety.

Fluid can be urged from the fluid reservoir 112 into the inner lumen 106 by a pump 116. In one embodiment, the pump 116 can be a syringe-type pump that produces a fixed volume flow via linear advancement of a plunger (not shown). In other embodiments, however, other types of pumps, such as a diaphragm pump, may also be employed.

The pump 116, as well as any other components of the system, can be controlled by a controller 118. The controller 118 can include a power supply 119 and can be configured to deliver electrical control signals to the pump 116 to cause the pump to produce a desired flow rate of fluid. The controller 118 can be connected to the pump 116 via an electrical connection 120. The controller 118 can also include an interface for receiving lead wires or other connecting elements to electrically couple the controller 118 to the elongate body 102 and one or more return electrodes 124. These electrical connections, which can have any desired length and can utilize any known electrical connecting elements to interface with the controller 118 (e.g., plugs, alligator clips, rings, prongs, etc.), are illustrated in FIG. 1 as connections 122 and 126. In addition, the controller 118 can be connected to the heating assembly 110 through a similar electrical connection, as described below.

The return electrode 124 can have a variety of forms. For example, the return electrode 124 can be a single large electrode located outside a patient's body. In other embodiments, the return electrode 124 can be a return electrode located elsewhere along the elongate body 102, or it can be located on a second elongate body introduced into a patient's body near the treatment site. In such an embodiment, one or more outlet ports can be included in the return electrode as well to provide enhanced fluid flow to the tissue surrounding the return electrode. Regardless of the configuration used, the return electrode 124 can be designed to receive current emitted from the ablation element 105, thereby completing the circuit back to the controller 118 through the electrical connection 126.

In operation, the controller 118 can drive the delivery of fluid into target tissue at a desired flow rate, the heating of the fluid to a desired therapeutic temperature, and the delivery of therapeutic ablative energy via the one or more ablation elements, such as electrode 105. To do so, the controller 118 can itself comprise a number of components for generating, regulating, and delivering required electrical control and therapeutic energy signals. In addition to the power supply 119 mentioned above, the controller 118 can include one or more digital data processors and associated storage memories that can be configured to perform a variety of functions, or control discrete circuit elements that perform a given function. These functions can include, for example, the generation of one or more electrical signals of various frequencies and amplitudes. Furthermore, the controller 118 can be configured to amplify any of these signals using one or more RF power amplifiers into relatively high-voltage, high-amperage signals, e.g., 50 volts at 1 amp. These RF signals can be delivered to the ablation element 105 via one or more electrical connections 122 and the elongate body 102 such that RF energy is passed between the emitter electrode 105 and any return electrodes or electrode assemblies 124 that are located remotely on a patient's body. In embodiments in which the elongate body is formed from non-conductive material, the one or more electrical connections 122 can extend through the inner lumen of the elongate body or along its outer surface to deliver current to the emitter electrode 105. Of course, in certain embodiments more than one emitter electrode can be included on one or more elongate bodies. The passage of RF energy between the ablation element (or elements) and the return electrode 124 (or return electrodes) can heat the fluid and tissue surrounding the elongate body 102 due to their inherent electrical resistivity. The controller 118 can also include a number of other components, such as a directional coupler to feed a portion of the one or more RF signals to, for example, a power monitor to permit adjustment of the RF signal power to a desired treatment level. The controller 118 can also include one or more components to monitor temperature of fluid delivered to tissue or tissue itself using, for example, one or more thermocouples or other sensors coupled to the elongate body or bodies. Still further, the controller 118 can include a user interface to allow an operator to interact with the controller and set desired therapy operating parameters or receive feedback from the controller (e.g., warnings, indications, etc.).

Figure 2A:
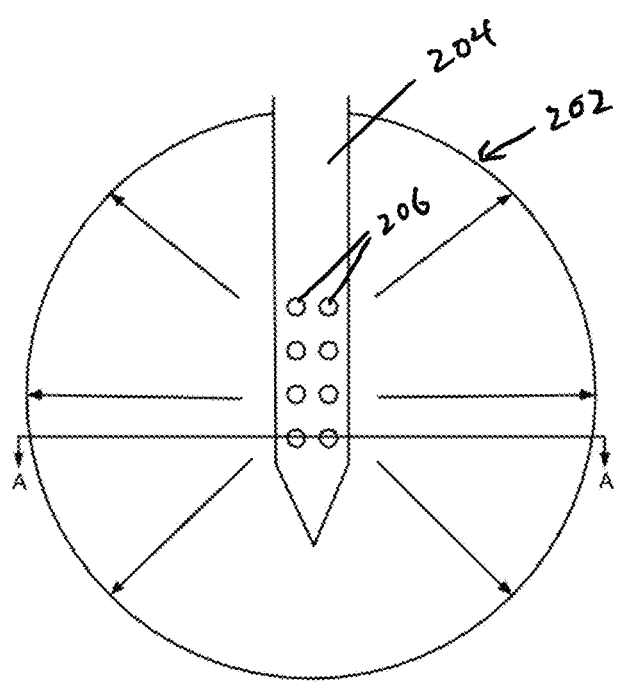
FIG. 2A is a side view of one embodiment of ideal fluid flow from an elongate body.
Figure 2B:
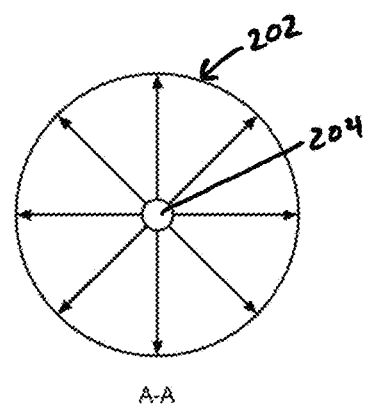
FIG. 2B is an end view of the fluid flow of FIG. 2A.

Because fluid enhanced ablation therapy relies upon fluid to convect heat through tissue and prevent dehydration or desiccation of tissue due to excess heating, it is desirable to have fluid flow through tissue wherever RF or other ablative energy is administered. While different desired flow patterns are possible, FIGS. 2A and 2B illustrate one embodiment of an ideal flow pattern in which a spherical flow of fluid 202 is created around an elongate body 204. Note that the ideal spherical flow 202 extends in every direction around a distal portion of the elongate body 204 that can include an ablation element. Accordingly, a central source of ablative energy can be concentrically located with the outlet ports 206 that originate the fluid flow 202. Tissue inside this volume can be treated with therapeutic levels of thermal energy, while also being constantly hydrated and regulated such that overheating (e.g., so-called "steam pops," which can occur when fluid in tissue is heated above 100° C.) and desiccation do not occur. With proper fluid flow, large volumes of tissue can be treated efficiently without requiring repositioning of the device.

In contrast, some prior art devices utilize a single outlet port at a distal end thereof to distribute fluid into tissue, or a series of outlet ports clustered close to a distal end of the device. This can create a fluid flow that originates a distance away from the ablative energy source (e.g., imagine shifting the fluid flow 202 down in the plane of the figure) and, as a result, can fail to deliver an adequate flow of fluid to certain areas receiving high concentrations of ablative energy. These areas of reduced fluid flow can become dehydrated and the resulting overheated tissue can desiccate and char, and can be accompanied by an attendant increase in tissue impedance that can effectively end the therapy.

Figure 3:
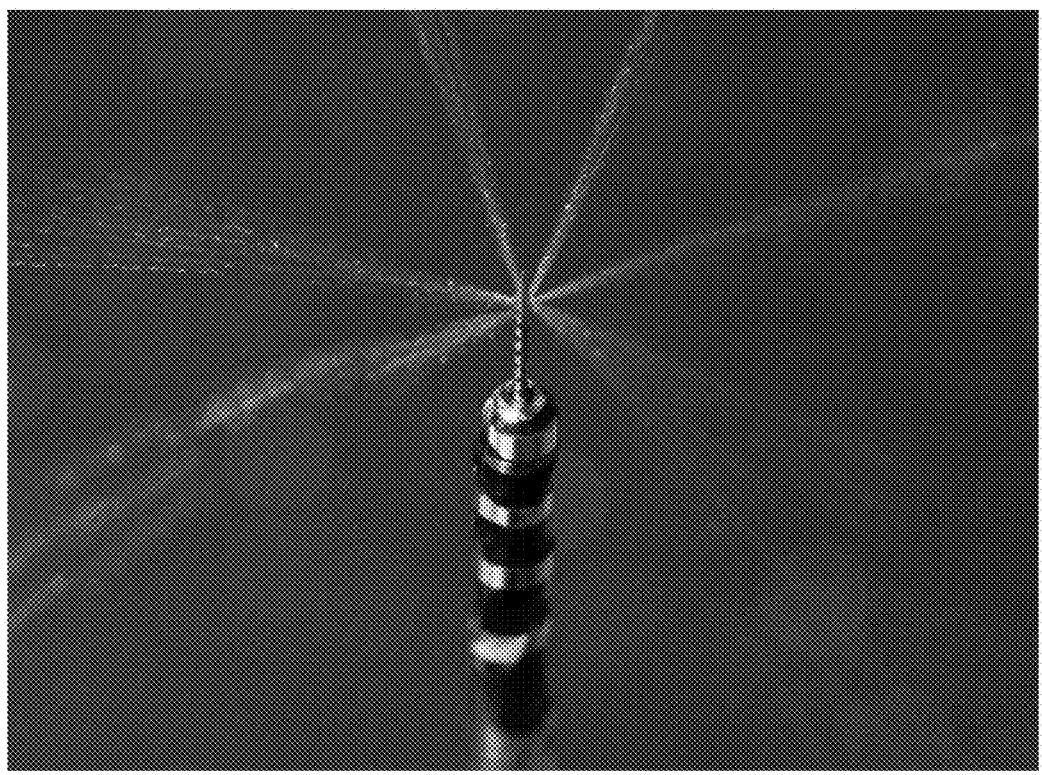
FIG. 3 is a photograph showing distally-biased fluid flow in air from a prior art elongate body.

Furthermore, the applicants of the present disclosure have discovered that, despite the disclosure of fluid distribution similar to the flow 202 described above, the elongate bodies and other devices, such as those described in U.S. Pat. No. 6,328,735 (and the other patents and publications mentioned herein), do not achieve the disclosed fluid distribution. FIG. 3 depicts one embodiment of an elongate body of the type described in these patents and publications and shows that it suffers from a distally-biased fluid flow pattern. Such a pattern likely performs better than a simple open distal end, but nevertheless suffers from insufficient proximal fluid flow that can result in overheating (e.g., steam pops), dehydration, and impedance rises in tissue adjacent to proximal portions of the elongate body.

More particularly, FIG. 3 is a photograph of an elongate body of the type described in U.S. Pat. No. 6,328,735 delivering fluid into air at a flow rate of about 50 ml/min. This flow rate is relatively high, but was utilized to achieve the streams shown in the photograph, as at lower flow rates in air fluid can appear to simply drip out of the distal end of the elongate body. As shown in FIG. 3, significant flow is achieved only from the distal-most outlet ports formed in the elongate body, indeed, nearly 100% of the fluid flow by volume is emitted from a distal-most 25% of outlet ports formed in the elongate body. Further details regarding this elongate body and its outlet port configuration are provided below and shown in FIG. 21. The pattern of outlet ports shown in FIG. 3 extends for approximately 4 mm, but only the distal-most 1 mm of outlet ports are producing significant fluid flow. As described above, this can mean that the tissue adjacent to the proximal 3 mm of outlet ports is insufficiently hydrated during therapy. Indeed, investigation into repeated occurrence of impedance rises and overheating in tissue adjacent to a proximal portion of an elongate body or ablation element led the applicants of the present disclosure to discover the depicted distally-biased flow.

To further illustrate the flow, and demonstrate that it is not present only at the relatively higher flow rate shown in FIG. 3, an elongate body of the same configuration was introduced into a bath of 37° C. saline and fluid containing an ultraviolet (UV) dye was delivered through the device. At flow rates ranging from about 5 ml/min to about 20 ml/min (rates at which fluid delivered into air would appear to be simply drops on the elongate body) a distal outlet port bias remained evident, with very low fluid flow velocity coming from the proximal outlet ports of the elongate body.

Figure 4:
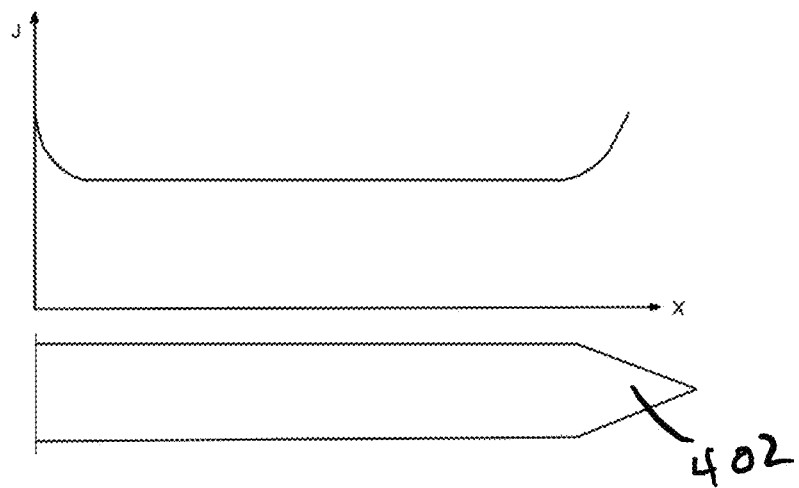
FIG. 4 is a diagram showing current density along one embodiment of an elongate body wherein the entire elongate body serves as an electrode.

Distal bias of fluid flow from an elongate body can be problematic during fluid enhanced ablation therapy because it can be different from a distribution of energy emitted from an ablation element of an elongate body. FIG. 4 illustrates one embodiment of an elongate body 402 that is formed from a conductive material and configured to deliver RF electrical energy into tissue. The elongate body 402 can be, for example, the above-described stainless steel needle disposed at a distal end of a catheter and configured to treat ventricular tachycardia with fluid enhanced ablation therapy. In such an embodiment, the entire elongate body can be the ablation element, as current can be passed from the elongate body through surrounding tissue to a collector electrode disposed remotely from the elongate body. As shown in the figure, the current density J emitted from the elongate body can spike near the distal tip and proximal end of the elongate body, and can be largely constant along its constant-diameter length. Accordingly, if fluid is hydrating tissue and regulating the temperature thereof only near a distal end of the elongate body 402, tissue adjacent a more proximal portion of the elongate body could easily overheat and dehydrate.

Figure 5:
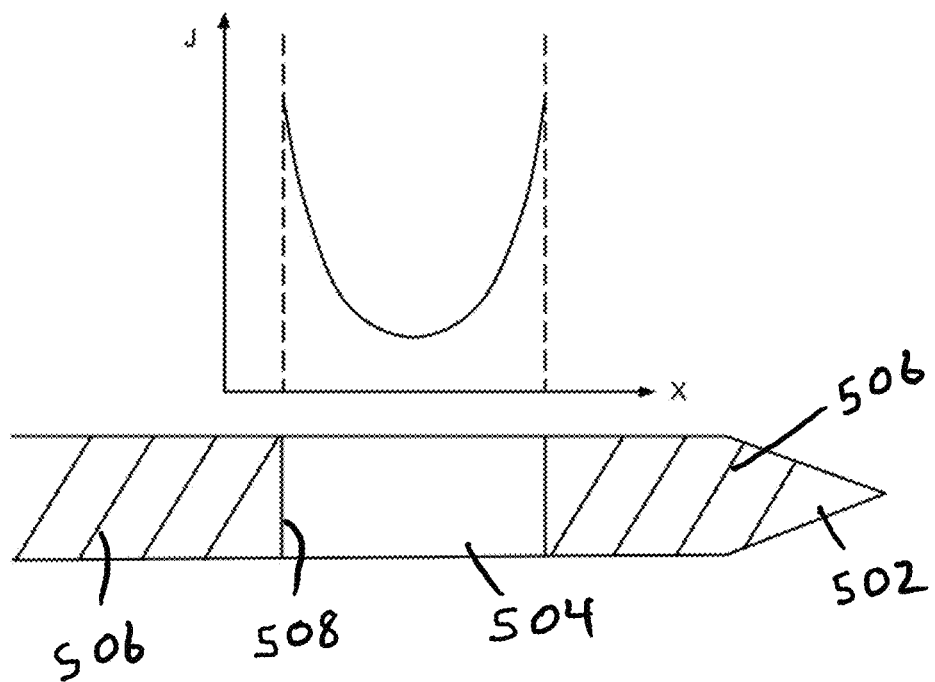
FIG. 5 is a diagram showing current density along one embodiment of an elongate body wherein an electrode is bounded by insulating shielding.

Moreover, this problem can be exacerbated by alternative elongate body configurations. FIG. 5, for example, illustrates one embodiment of an elongate body 502 that includes an ablation element 504 disposed along, or made up from, only a portion of the elongate body. This might be the case, for example, in the above-described stainless steel needle configured for laparoscopic or percutaneous insertion into a patient's body. Such a device can be, for example, covered in an electrically insulating shielding 506 along all but a portion of its length. The exposed portion of conductive steel can be utilized as the ablation element 504 in the form of, again, an RF electrode.

The graph of FIG. 5 illustrates the current density J along the length of the elongate body 502. Note that the current density rises significantly at the edges, or boundaries, of the ablation element 504. This significant increase in current density can be particularly problematic for the proximal boundary 508 of the ablation element 504 if insufficient fluid is delivered at this location. This is especially true because the heating experienced in adjacent tissue is related to the square of the illustrated current density.

Addressing the problem of distally-biased flow might appear at first to be simple, as intuition would suggest that the addition of more outlet ports, thus reducing outflow resistance, would produce more flow. However, the applicants of the present disclosure have discovered that, counterintuitively, the addition of more outlet ports does not improve the distribution of fluid flow. Just the opposite, the applicants of the present disclosure have discovered that the addition of flow resistance to the elongate body results in better distributed flow from each of the outlet ports. Flow resistance can encompass more than one concept of resistance to fluid flow. For example, flow resistance as used herein can refer to resistance to fluid flow per unit length of lumen, which can be exemplified by reducing a diameter of an inner lumen along a length of an elongate body, among other things. Flow resistance can also refer to resistance to fluid flow from an elongate body lumen into tissue surrounding the elongate body, e.g., resistance to flow through one or more outlet ports. The idea that adding flow resistance to the elongate body would create more uniform flow from all outlet ports was unexpected, as it runs counter to the intuitive response to the problem.

The addition of flow resistance can be accomplished in a number of manners that are discussed in more detail below. By way of example, flow resistance can be increased by reducing the number of outlet ports formed in the elongate body, by reducing the area of each port or changing their shape, or by otherwise adding features to the inner lumen of the elongate body to increase flow resistance. These modifications can all function to increase fluid pressure within the inner lumen along a length of the elongate body that contains the outlet ports. Another way to think of the increased flow resistance is in terms of fluid stall pressure—the goal being to stall fluid flow farther back into the elongate body proximally beyond the location of all outlet ports. Doing so can result in fluid flowing out uniformly from all of the outlet ports, or in a predetermined non-uniform manner if so desired.

Figure 6:
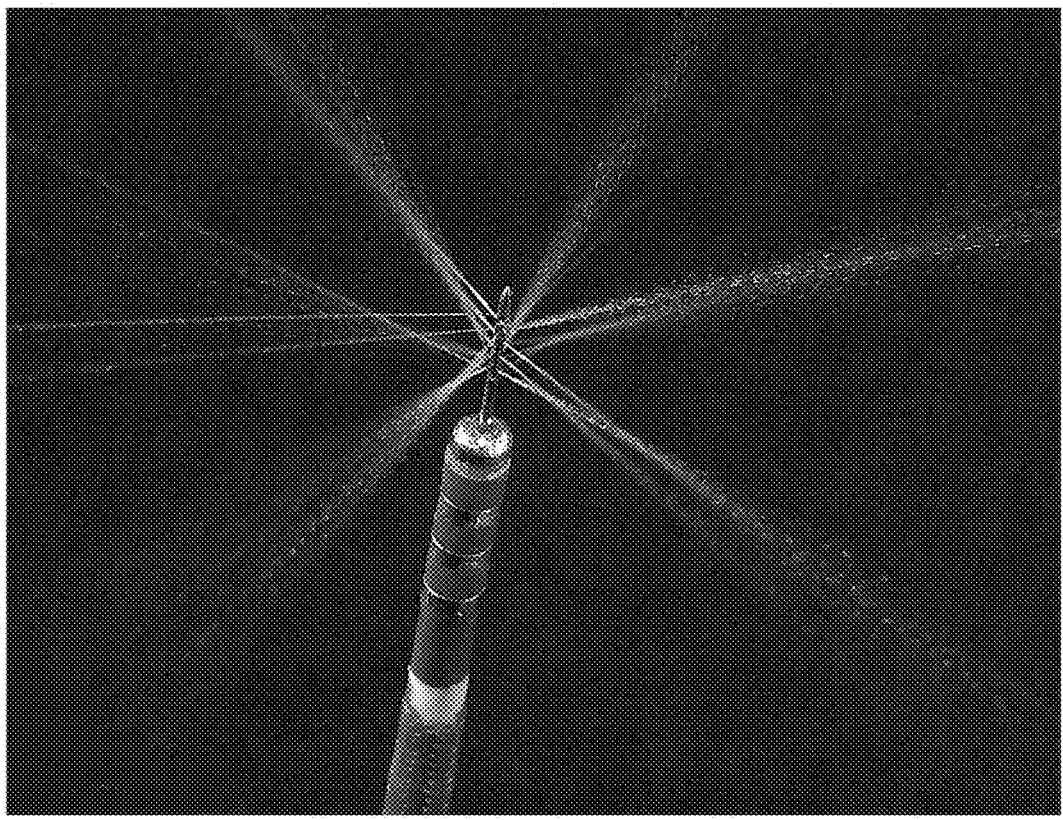
FIG. 6 is a photograph showing uniform fluid flow in air from an elongate body according to the teachings of the present disclosure.

In connection with the unexpected and counterintuitive discovery that increasing flow resistance can result in better flow from all of the outlet ports, the applicants of the present disclosure have discovered that in some embodiments a ratio of the cumulative area of all outlet ports (i.e., a cross-sectional area) in relation to an area of the inner lumen (i.e., a cross-sectional area) can be used to select appropriately sized elongate bodies and outlet port configurations that produce desired fluid flow from each outlet port. FIG. 6 illustrates one embodiment of an elongate body according to the teachings of the present disclosure delivering fluid into air at a same flow rate as the elongate body depicted in FIG. 3. The additional flow resistance resulting from selection of outlet port size in relation to inner lumen size can produce the uniform flow from each outlet port shown in FIG. 6.

Figure 7A:
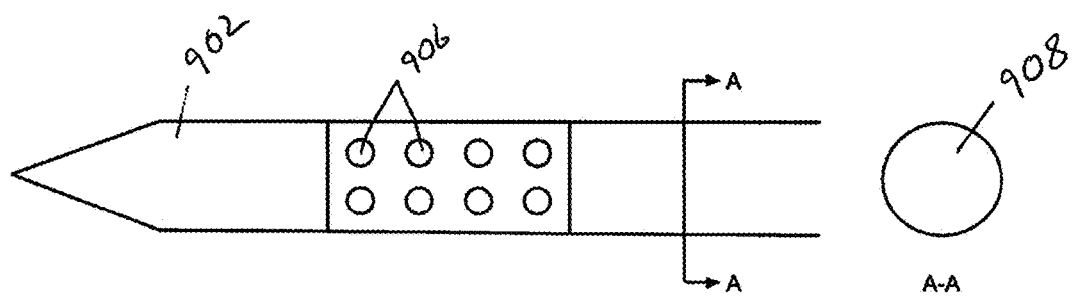
FIG. 7A is a diagram of one embodiment of an elongate body according to the teachings of the present disclosure.
Figure 7B:
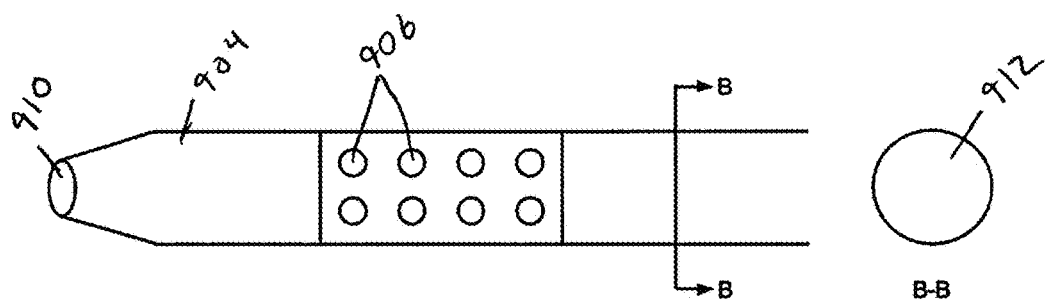
FIG. 7B is a diagram of an alternative embodiment of an elongate body according to the teachings of the present disclosure.

FIGS. 7A and 7B illustrate two embodiments of an elongate body 902, 904 and how the ratio can be applied.

With regard to FIG. 7A, the ratio can be calculated by summing the area of each outlet port 906 (i.e., summing the cross-sectional area of the eight outlet ports visible in the figure plus the area of any outlet ports hidden from view) and comparing it to the area of the inner lumen 908. In some embodiments, the cross-sectional area of the inner lumen 908 can be taken at a point of maximum diameter or, in some embodiments, at a point just proximal to the proximal-most outlet port (in many embodiments, the elongate body can have a maximum diameter at the point just proximal to the proximal-most outlet port). To ensure proper distribution of fluid flow from each outlet port 906, this ratio can be kept below about 3:1. In some embodiments, the ratio can be kept below about 2.5:1, while in other embodiments the ratio can be kept below about 2:1. In certain embodiments, the ratio can be kept between about 0.5:1 and about 2:1, which is roughly equivalent to the mathematical relationship of 1×/÷2 (1 times or divide by 2). In still other embodiments, it can be desirable to keep the ratio around about 1.3:1, or even around about 1:1. As a point of comparison, the ratio for the elongate bodies of the type disclosed in the prior art and depicted in FIG. 3 is on the order of 6:1, far above the range set out above that can ensure proper fluid flow distribution.

The ratio can hold true regardless of the configuration of outlet ports found in the device. For example, the ratio can be maintained with the elongate body 904 of FIG. 7B, despite the fact that a large distal end opening 910 is present in addition to the plurality of outlet ports 906. When computing the total area of the outlet ports, the cross-sectional area of the opening 910 can be added to the cross-sectional areas of the outlet ports 906. So long as the ratio of this total outlet area to the cross-sectional area of the inner lumen 912 remains below about 3:1, fluid should flow from each outlet port 906 and the opening 910.

Figure 8:
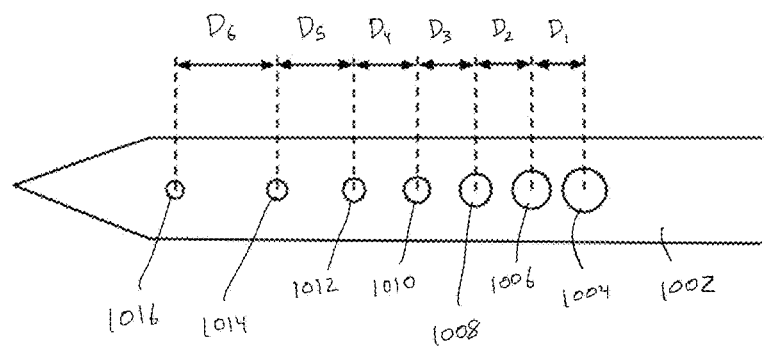
FIG. 8 is a diagram of one embodiment of an elongate body having varying outlet port spacing and outlet port cross-sectional area.

Another mechanism for adjusting flow resistance can be adjusting the size and relative spacing of the ports. FIG. 8 illustrates one embodiment of an elongate body 1002 with a plurality of outlet ports 1004-1016 having varying sizes and relative spacing. In the illustrated embodiment, a diameter of the outlet port 1004 is larger than a diameter of any more distal outlet port 1006-1016. By decreasing the size of the outlet ports 1004-1016 as they proceed from a proximal end of the elongate body 1002 to a distal end thereof, increased pressure can be built up within a distal portion of the inner lumen of the elongate body while pressure required to produce flow for the proximal-most outlet ports 1004, 1006, etc. can be minimized.

In addition to varying the size of the outlet ports 1004-1016, their relative spacing (e.g., as measured axially along a longitudinal axis of the elongate body, angularly around a circumference of the elongate body, or combinations thereof) can also be varied along a length of the elongate body 1002. In some embodiments, this variation can be inverse to the variation described above with respect to outlet port diameter or size. In other words, spacing between adjacent outlet ports or successive rows of outlet ports spaced around an elongate body, can increase from a proximal end of the elongate body 1002 to a distal end thereof. Accordingly, the distance $D_1$ can be less than any distance $D_2$-$D_6$ positioned distally thereof. Such an arrangement clusters additional (and possibly larger) outlet ports near a proximal end of the elongate body 1002, thereby promoting flow in this area and building additional fluid pressure in a distal portion of the inner lumen.

FIG. 8 illustrates a single row of axially aligned outlet ports 1004-1016, but outlet ports can often be created by forming a series of through-holes (thereby creating two opposed outlet ports) at angular and axial offsets from one another, as shown by FIGS. 21, 22, 24, and 26, described in more detail below. As noted above, in some embodiments the angular offset of outlet ports can also be varied to further adjust the pattern and distribution of fluid flow.

Figure 9A:
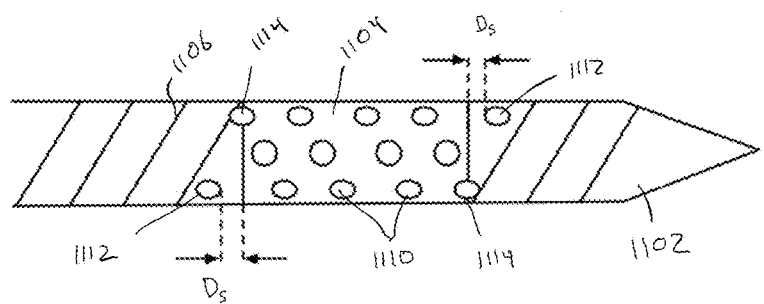
FIG. 9A is a diagram of an alternative embodiment of an elongate body according to the teachings of the present disclosure.

Still further, in some embodiments one or more outlet ports can be specifically positioned to enhance fluid flow at a desired location. FIG. 9A, for example, illustrates one embodiment of an elongate body 1102 having an ablation element 1104, such as an RF electrode, disposed along a length thereof and bounded at proximal and distal ends. Ablation element boundaries can be created in a number of manners, including, for example, with electrically insulating shielding 1106 disposed around the elongate body along its proximal and distal ends. A plurality of outlet ports 1110 are formed in the ablation element 1104 and a current density along a length of the ablation element 1104 can be similar to the current density depicted in FIG. 5. To aid in hydrating and regulating the heating of tissue adjacent to the boundaries of the ablation element 1104, the elongate body 1102 can include one or more outlet ports 1112 positioned at least partially outside the boundary of the ablation element 1104 on a proximal and/or distal end thereof. The one or more outlet ports 1112 can be separated from the ablation element boundary by a distance $D_5$. In addition, one or more outlet ports 1114 can be included that straddle a boundary of the ablation element 1104. The placement, size and other characteristics of these additional outlet ports can be determined in line with the design rules outlined above regarding area ratio, proximal-to-distal decrease in size, and proximal-to-distal increase in relative spacing.

Figure 9B:
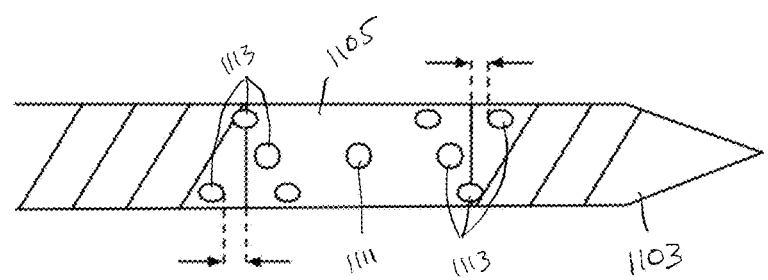
FIG. 9B is a diagram of another embodiment of an elongate body according to the teachings of the present disclosure.

In some embodiments, the addition of outlet ports in the vicinity of an electrode or other ablation element boundary can be balanced with a reduction of outlet ports along a central portion of the ablation element. FIG. 9B illustrates one embodiment of an elongate body 1103 that includes an ablation element 1105 that is bounded by proximal and distal ends, similar to the elongate body 1104. Also similar to the elongate body 1104, the elongate body 1105 can include a plurality of outlet ports formed therein, including a clustering of outlet ports 1113 positioned near to and/or at least partially outside the boundary of the ablation element 1105. In contrast to the elongate body 1104, however, the elongate body 1105 includes fewer outlet ports 1111 formed in a central portion of the ablation element 1105. By arranging the outlet ports in this manner, the fluid distribution pattern can be adjusted to match, for example, the energy distribution pattern present in the tissue (e.g., as shown in FIG. 5).

Figure 10A:
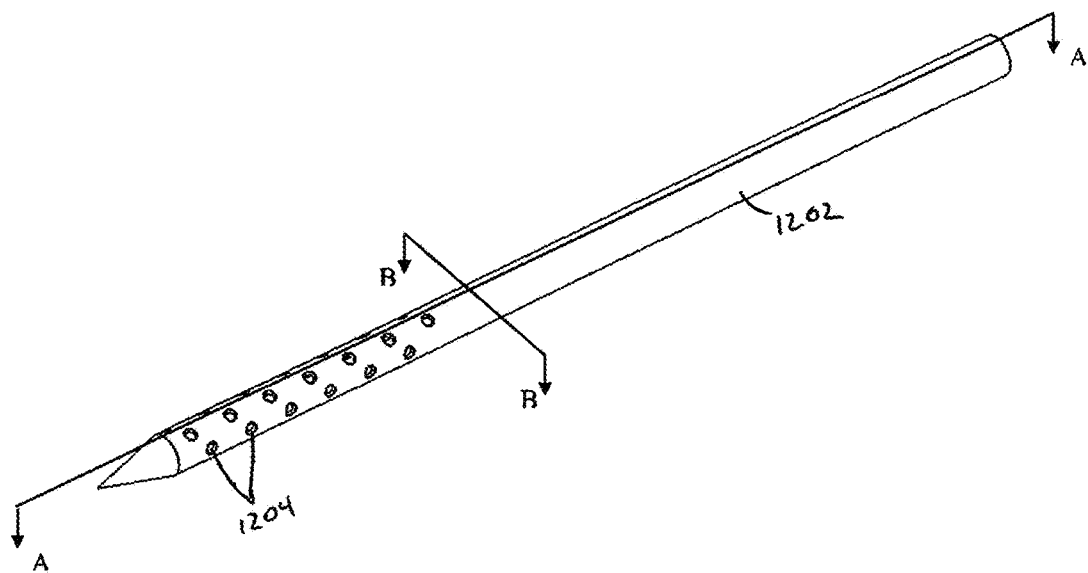
FIG. 10A is a perspective view of one embodiment of an elongate body including a flow diverter.
Figure 10B:
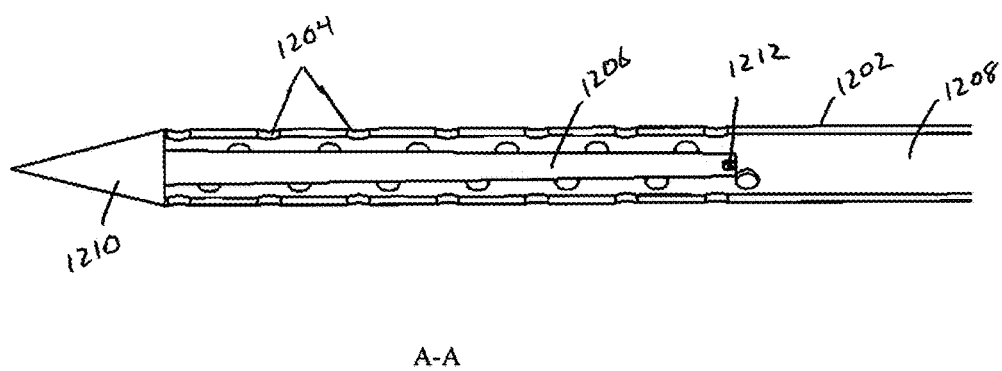
FIG. 10B is a cross-sectional view of the elongate body of FIG. 10A along line A-A.
Figure 10C:
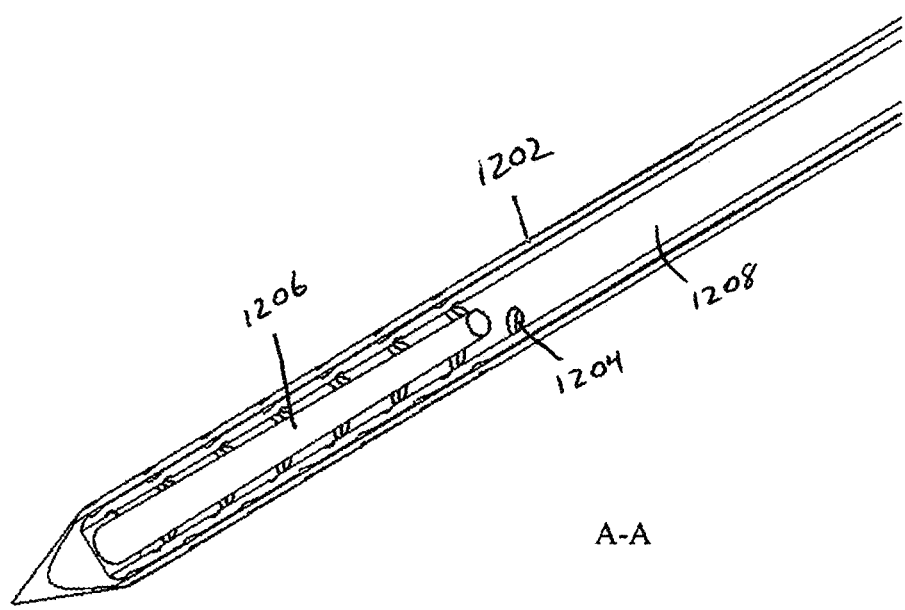
FIG. 10C is an alternative cross-sectional view of the elongate body of FIG. 10A along line A-A.
Figure 10D:
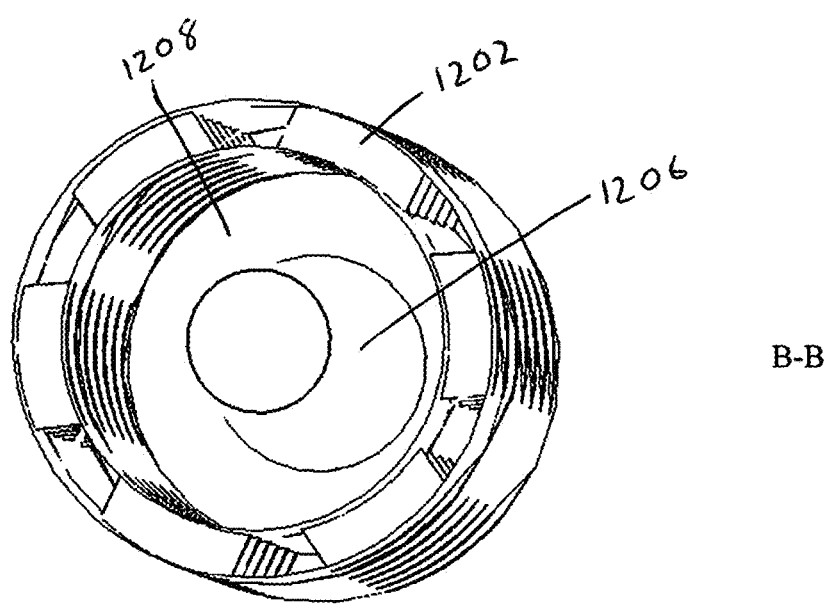
FIG. 10D is a cross-sectional view of the elongate body of FIG. 10A along line B-B.

Increasing flow resistance can be accomplished in a number of manners, not all of which require changing characteristics of the outlet ports themselves. Another way to increase flow resistance per unit length of lumen through a plurality of outlet ports can be to reduce the cross-sectional flow area of an inner lumen of an elongate body from a proximal end to a distal end of the elongate body, or of a portion of the elongate body containing outlet ports. FIGS. 10A-10D illustrate one embodiment of an elongate body 1202 having a plurality of outlet ports 1204 and a tapered flow diverter 1206 disposed in an inner lumen 1208 of the elongate body. The flow diverter 1206 can have a conical shape, such as the illustrated truncated cone shape. The diverter 1206 can be positioned within the inner lumen 1208 such that it is concentric with the inner lumen, as shown in FIGS. 10C and 10D. In the illustrated embodiment, the flow diverter 1206 is attached to the elongate body 1202 at its distal end 1210, which, as described above, can be a solid terminus in certain embodiments.

The truncated cone shape of the flow diverter 1206 can serve to progressively reduce the area of the inner lumen from its proximal to its distal end. This, in turn, progressively reduces the cross-sectional flow area of the inner lumen in the same direction. The reduction in area at the distal end of the elongate body 1202 can increase the fluid pressure at this end and cause fluid flow to stall farther back proximally into the inner lumen 1208. As explained above, increasing the fluid pressure within the inner lumen of an elongate body can promote flow from proximally-positioned outlet ports and ensure a more uniform distribution of fluid from all of the outlet ports.

The flow diverter 1206 can be formed from a variety of materials and its dimensions can be largely influenced by the elongate body into which it fits. In some embodiments, for example, the flow diverter can be formed from stainless steel in the same manner as the elongate body. Further, the flow diverter 1206 can be utilized as a mounting location for one or more sensors to monitor characteristics of the flow within the inner lumen 1208. By way of example, a thermocouple 1212 can be positioned at a proximal end of the flow diverter and can monitor the temperature of saline or other fluid just before it is delivered to tissue through the outlet ports. In some embodiments, the heating assembly 110 described above can also be positioned at the proximal end of the flow diverter.

Figure 11:
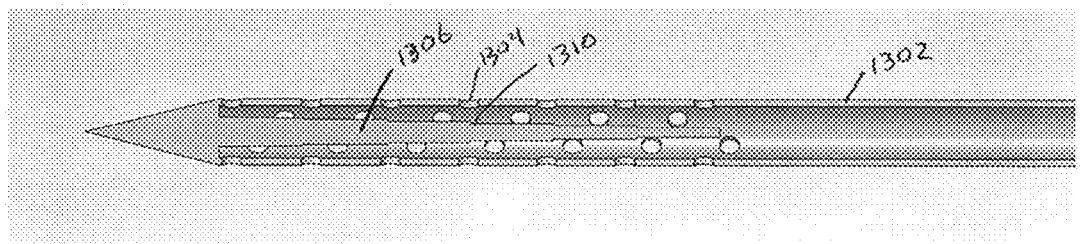
FIG. 11 is a cross-sectional view of one embodiment of an elongate body including a flow diverter having one or more steps.

The flow diverter 1206 can have a number of configurations, including different shapes, according to the desired impact on fluid flow. One possible variation on the smooth truncated cone shape of the flow diverter 1206 is illustrated in FIG. 11, which includes a stepped cone flow diverter 1306 having 90° transitions from one diameter to another. Features formed on the flow diverter, such as step 1310, can have an effect on flow performance, especially when the step 1310 or other feature is aligned with one or more outlet ports 1304. Such effect can be due to the physical redirection of flow that can occur when fluid encounters, for example, a 90° transition at the step 1310.

Given their effect on flow, steps can be strategically positioned in some embodiments to provide desired flow characteristics. For example, steps can be placed wherever more forceful delivery of fluid is desired. This can include, for example, placing steps to aid in biasing a flow pattern toward a proximal end of the elongate body. This is one example, however, as a number of other flow pattern shapes can be achieved by varying the placement of steps or other surface features on a flow diverter.

Moreover, steps 1310 need not be symmetrical or uniform along the length or circumference of the flow diverter 1306. In some embodiments, localized features such as steps, ridges, bumps, cones, pins, etc. can be formed on the surface of the flow diverter 1306. Or a plurality of smaller flow diverters can be formed on sidewalls of the inner lumen of the elongate body 1302, e.g., just proximally of individual outlet ports 1304. Alternatively, the flow diverter 1306 can include a winding form, such as a helix or screw thread.

In still other embodiments, the flow diverter 1306 or inner lumen sidewalls can include features to selectively reduce pressure and flow output. For example, one or more recesses formed in the flow diverter 1306 can cause a localized pressure drop which, if aligned with an outlet port, can cause flow through the outlet port to be reduced. Such recesses can be utilized in some embodiments to accumulate fluid whose flow is being controlled farther downstream in the device (i.e., distally of the recess or recesses). In certain embodiments, such recesses or other pressure reduction features can be used in combination with steps or other features to create turbulence within the fluid flow. This can be useful, for example, to enhance fluid mixing and distribute energy delivered to the fluid from a heating element (e.g., heating assembly 110 described above).

Figure 12:
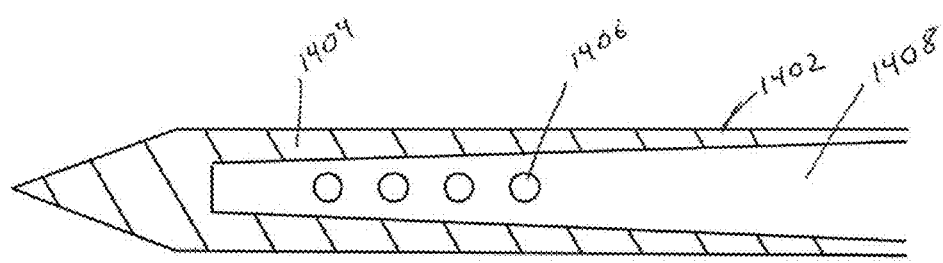
FIG. 12 is a cross-sectional view of one embodiment of an elongate body including a tapered inner diameter.

The embodiments described above make use of a flow diverter feature disposed concentrically within an inner lumen of an elongate body that functions to reduce the cross-sectional flow area of the inner lumen and build fluid pressure. In some embodiments, however, the same effect can be accomplished without the use of a pin or other diverter feature centrally disposed in the inner lumen. FIG. 12 illustrates one embodiment of an elongate body 1402 that includes tapered sidewalls 1404 that progressively increase in thickness from a proximal end to a distal end of the portion of the elongate body containing outlet ports 1406. The taper of the sidewalls 1404 can reduce the diameter, and hence the cross-sectional area of the inner lumen 1408 of the elongate body 1402 toward a distal end thereof, thereby increasing fluid pressure within the inner lumen in the same manner as the flow diverter pins discussed above. Any number of the features discussed above, including steps, ridges, or other protrusions, as well as recesses or other pressure reduction features, can be formed on the tapered sidewalls 1404 in the same manner as the flow diverters 1206, 1306.

Figure 13:
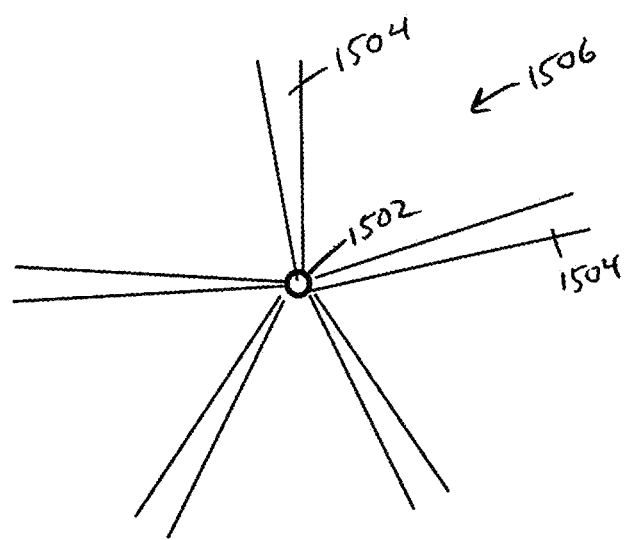
FIG. 13 is an end view diagram of one embodiment of fluid flow from an elongate body.

As noted above, outlet flow distribution can be modified by adjusting the size and spacing of the ports themselves, as well as by including one or more flow diverting features within an inner lumen of an elongate body. It can also be desirable in some cases to adjust the shape of the outlet ports in order to further modify the flow distribution pattern. FIG. 13 illustrates a front view of one example of an elongate body 1502 of the type described above. The elongate body 1502 (a distal end of which is visible in the figure) can include a plurality of outlet ports that are circular in shape and spaced around the circumference of the elongate body. As a result, the flow distribution pattern can appear like a wheel hub having a number of spokes or cones 1504 of fluid extending therefrom. This distribution pattern can include gaps 1506 between adjacent cones of fluid 1504. When attempting to create a fluid flow like that shown in FIGS. 2A and 2B, i.e., a spherical pattern, such gaps can be undesirable. This is because tissue in the gaps 1506 can receive relatively lower amounts of fluid than tissue directly in the path of the fluid 1504. In addition, tissue in the path of the fluid 1504 can experience elevated pressure from the strong flow passing directly therethrough.

Figure 14:
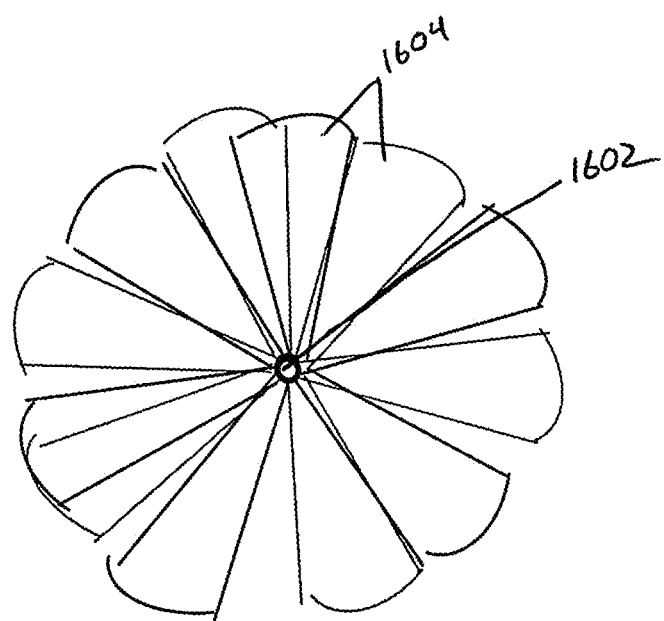
FIG. 14 is an end view diagram of an alternative embodiment of fluid flow from an elongate body.

To eliminate gaps and provide a more even distribution of fluid in tissue, one solution can be to vary the shape of the outlet ports such that fluid emitted therefrom travels in a different pattern. For example, circular outlet ports can be replaced with slots that create more of a fan-shaped fluid flow pattern. FIG. 14 illustrates one embodiment of fluid flow that can result if outlet ports are slot-shaped, rather than circular. As with FIG. 13, a distal end of an elongate body 1602 is visible, along with a plurality of fan-shaped fluid flows 1604 extending therefrom. More specifically, this embodiment makes use of two staggered rows of six slots. The length of the slots, as well as the degree of overlap between slots in different rows can be adjusted to minimize the number of gaps present in the flow pattern.

This type of fluid distribution pattern can have a number of advantages over the flow depicted in FIG. 13. As already noted, for example, the number and size of gaps in the fluid flow pattern can be minimized. In addition, mechanical stresses on tissue can be reduced, as no tissue encounters the concentrated spoke-like flow of FIG. 15. Moreover, therapy performance can be improved, especially at lower flow rates, because the target volume of tissue surrounding the elongate body can be perfused with fluid without excess backfill that can be created by concentrated radial spoke-like flow.

FIGS. 15A-19 illustrate a number of embodiments of outlet ports shapes, as well as patterns for overlaying outlet ports to produce interlaced flow patterns that minimize or eliminate gaps. FIG. 15A illustrates a side view of an elongate body 1702 having a pattern of circular or round outlet ports 1704, similar to the other embodiments described above. FIG. 15B introduces a single row of slot-shaped outlet ports 1706 to the pattern of FIG. 15A. The slot-shaped outlet ports 1706 can be positioned centrally along a length of a portion of the elongate body 1702 containing outlet ports, such that the slots can help create a strong equator or central waist of a spherical flow pattern. In other embodiments, additional rows of slot-shaped outlet ports can be included, or individual slot-shaped outlet ports can be interspersed within the pattern of circular outlet ports.

FIG. 16A illustrates an alternative embodiment of a slot-shaped outlet port 1806 in which an S-curve shape is utilized. FIGS. 16B and 16C similarly illustrate possible combinations of multiple rows of slot-shaped outlet ports 1808-1814 in relation to circular (or other non-circular) outlet ports 1704. For example, rows of slot-shaped outlet ports can be utilized at proximal and distal ends of the outlet ports in addition to a central waist, as in FIG. 16B, or at proximal and distal ends without a central waist, as in FIG. 16C. In addition, rows of outlet ports (whether circular, slot-shaped, or otherwise) can be formed in rings around an elongate body, as shown in the figures, or in alternative shapes, such as a helix, etc.

Individual outlet ports can have any of a variety of shapes, including straight slots, S-shaped curves, keyhole slots, comma-shaped openings, teardrop-shaped openings, or hybrids thereof. FIG. 17 illustrates one example of a hybrid circular and slotted outlet port 1902. The outlet port 1902 includes a circular central portion 1904 and opposed curved slot-shaped appendages 1906, 1908. Slot-shaped outlet ports can have any variety of shapes that include an aspect ratio in which, for example, a length of the outlet port is greater than a width thereof.

Such outlet ports can be formed in an elongate body using any suitable manufacturing technique. For example, outlet ports can be formed using laser cutting, mechanical stamping, routing, etc. Outlet port shape, size, and spacing can be selected so as to minimize mechanical degradation of the elongate body while ensuring that 360° fluid distribution coverage (or any alternative desired coverage) is achieved.

FIG. 18A illustrates another embodiment of a diagonal row of outlet ports 2002 composed of two offset straight slots that connect along a portion of their length. This shape somewhat approximates the shape shown in FIG. 17, with a larger central opening and two slot-shaped appendages extending therefrom. FIG. 18B illustrates a similar row of outlet ports 2003, but the outlet ports in this figure include round openings at each end that are connected by a curved slot. The inclusion of a circular feature at an end (e.g., a proximal or leading end) of a slot can help to initiate flow through the slot.

Figure 19:
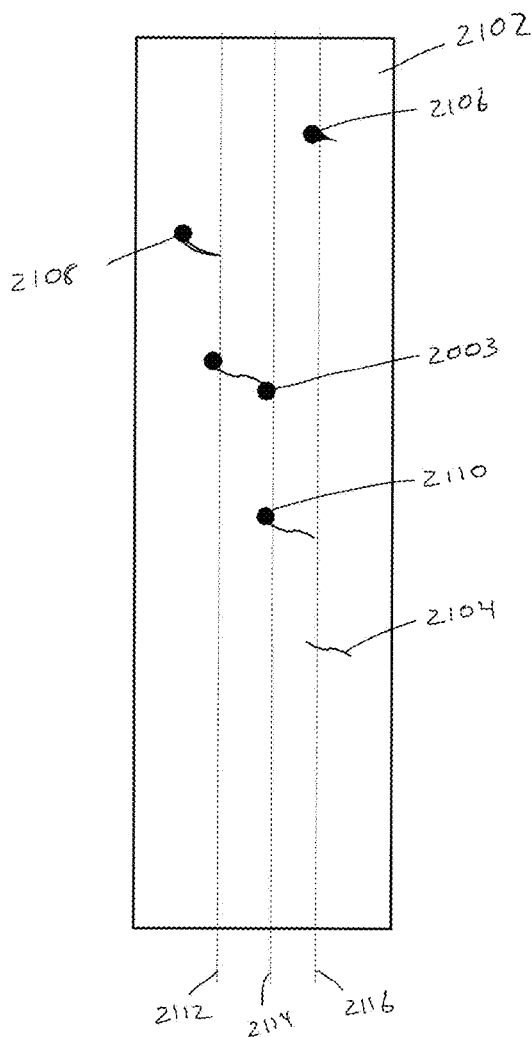
FIG. 19 is a side view of another embodiment of an outlet port pattern of an elongate body showing axial overlap of various outlet ports.

FIG. 19 illustrates another embodiment of an elongate body 2102 that includes various outlet port shapes. For example, an outlet port 2003 like that shown in FIG. 18B can be disposed centrally, along with a curved slot outlet port 2104, a teardrop outlet port 2106, and two outlet ports 2108, 2110 including a circular portion and a trailing slot-shaped portion. Also shown in FIG. 19 are axial overlay lines 2112,

2114, 2116. These lines help illustrate where flow from, for example, outlet ports 2108 and 2003 would overlap if the flow pattern were observed from a distal end of the elongate body 2102 (similar to the views shown in FIGS. 13 and 14).

Figure 20:
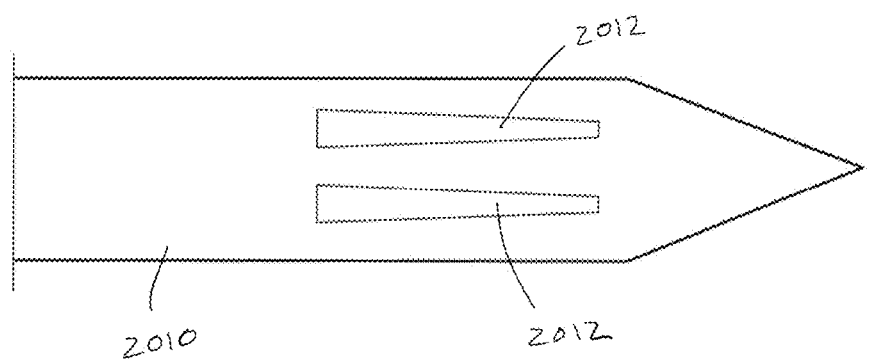
FIG. 20 is a side view of another embodiment of an outlet port pattern of an elongate body according to the teachings of the present disclosure.

FIG. 20 illustrates still another embodiment of an elongate body 2010 that includes outlet ports 2012 in the form of elongated slots. The outlet ports 2012 can have any of a number of variations from the shape in the figure, but in some embodiments can have a width that tapers from a proximal end of the slot to a distal end of the slot. This can be analogous to the distally-decreasing outlet port diameters shown in FIG. 8. The outlet ports can have a variety of different widths and lengths. In one embodiment, the length of each outlet port 2012 can be about 6 mm. Further, any number of these outlet ports 2012 can be formed in the elongate body 2010 around a circumference thereof.

The above description makes clear that any number of different outlet port shapes and layouts along the surface of an elongate body are possible to tailor a fluid flow pattern. The pattern can be adjusted to create a uniform, radial flow surrounding the elongate body or to create any other shape of flow pattern, or to bias the pattern toward a proximal or distal end of the elongate body. It should be noted, however, that regardless of the outlet port shapes utilized, the above described guidelines regarding the total outlet port surface area in relation to the inner lumen area can be respected to ensure that fluid flows in a desired manner from all of the outlet ports.

Figure 21:
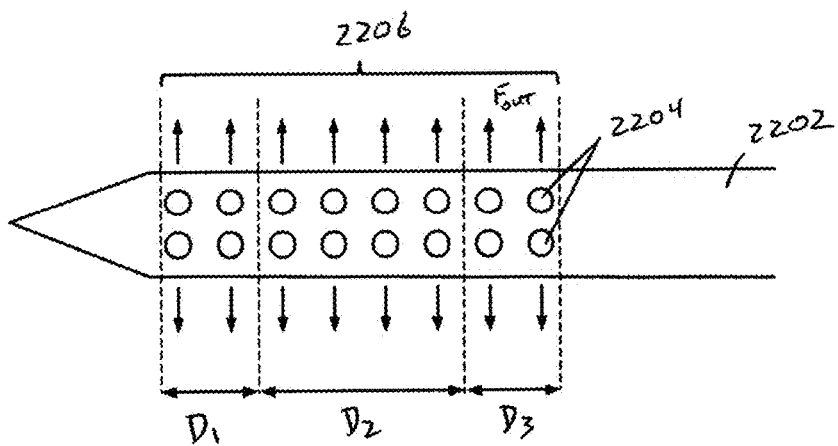
FIG. 21 is a diagram of one embodiment of an elongate body according to the teachings of the present disclosure.

Using the above described techniques, it can be possible to ensure desired fluid distribution from an elongate body during therapy. In particular, it can be possible to prevent the distally-biased flow phenomenon depicted in FIG. 3 that is associated with the elongate bodies described in prior publications. Of course, it can also be possible to prevent a proximally-biased flow distribution, or a centrally biased flow distribution. In some embodiments, fluid flow can be uniformly distributed along a fluid delivery portion of the elongate body that includes outlet ports. In other embodiments, fluid flow can be biased to any desired portion of the fluid delivery portion of the elongate body, but without depriving other portions of fluid flow to the degree seen, for example, in FIG. 3. FIG. 21 illustrates one example of a possible fluid flow distribution. The elongate body 2202 includes a plurality of outlet ports 2204 distributing fluid (as depicted by arrows $F_{out}$) that is delivered through an inner lumen of the elongate body. The outlet ports 2204 can be distributed along a fluid delivery portion 2206 of the elongate body 2202 that contains the outlet ports 2204. Using the techniques described herein, for example, the elongate body 2202 and outlet ports 2204 can be configured such that the flow from the outlet ports 2204 is substantially uniform or distributed as desired for a particular purpose. For example, in some embodiments less than about 70% by volume of the fluid delivered from all of the outlet ports 2204 can be emitted from those outlet ports that are disposed in a distal 25% of the fluid delivery portion 2206, i.e., those outlet ports disposed along distance $D_1$. Similarly, in some embodiments less than about 70% by volume of the fluid delivered from all of the outlet ports 2204 can be emitted from those outlet ports that are disposed in a proximal 25% of the fluid delivery portion 2206, i.e., those outlet ports disposed along distance $D_3$. Further, in some embodiments less than about 70% by volume of the fluid delivered from all of the outlet ports 2204 can be emitted from those outlet ports that are disposed in a central 50% of the fluid delivery portion 2206, i.e., those outlet ports disposed along distance $D_2$. Other fluid distribution patterns are possible, of course. In some embodiments, for example, the percentage of fluid by volume distributed from any of the distances $D_1$, $D_2$, or $D_3$ can be about 55%, about 40%, about 25%, or another value that creates a desired fluid distribution. For example, in some embodiments less than about 33% of all fluid delivered to tissue can be emitted from the outlet ports disposed in a distal 20% of the fluid delivery portion, etc. In still other embodiments, the outlet ports 2204 can be configured such that more than a certain percentage of fluid by volume is delivered from a certain subset of the outlet ports. For example, in some embodiments the outlet ports 2204 can be configured such that more than a predetermined percentage of fluid by volume is emitted from, for example, the central 50% of the outlet ports (i.e., along distance $D_2$ in FIG. 21). The predetermined percentage can be about 25%, about 35%, about 45%, about 55%, or some other desired value in various embodiments.

The teachings provided herein can also be applied to methods of ablating tissue that make use of, for example, embodiments of the elongate bodies described above. For example, in some embodiments a method of ablating tissue can include inserting an elongate body into a mass of tissue and delivering fluid into the tissue mass from a plurality of outlet ports formed along a fluid delivery portion of the elongate body. The method can also include delivering ablative energy into the tissue mass from an ablation element that is also inserted into the tissue mass and can be, for example, disposed along a length of the elongate body. Further, delivering fluid into the tissue mass can include, for example, delivering less than about 70% by volume of the fluid delivered to tissue from outlet ports disposed in a distal 25% of the fluid delivery portion of the elongate body. In other embodiments, the percentage delivered from the distal-most 25% of outlet ports can vary. For example, the percentage delivered from the distal-most 25% of outlet ports can be about 55%, about 40%, about 25%, or some other value that creates a desired fluid distribution pattern.

The devices disclosed herein can be designed to be disposed after a single use, or they can be designed for multiple uses. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present disclosure.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the device due to the materials utilized, the presence of electrical components, etc.

Experiments

The applicants of the present disclosure conducted experiments to evaluate various configurations of elongate bodies according to the teachings provided herein in comparison to those known in the art. Examples of embodiments considered include those described below.

Figure 22:
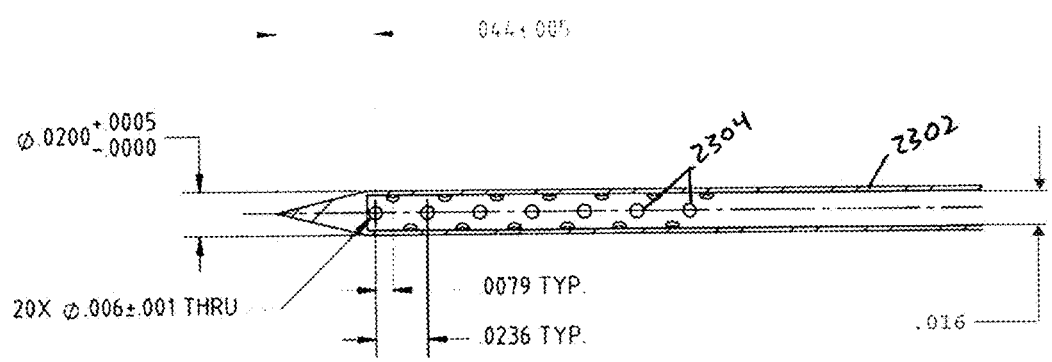
FIG. 22 is a side cross-sectional view of a prior art elongate body.

FIG. 22 illustrates an elongate body 2302 of the type described in prior publications and denoted as the "original" or "O" configuration in the data described below. The elongate body 2302 has an outer diameter of about 0.51 mm, an inner diameter of about 0.41 mm, and includes 20 through-holes formed therein, which result in the creation of 40 total outlet ports 2304 that are each circular and have a diameter of about 0.15 mm (dimensions shown in the figure are in inches). A resulting ratio of total outlet port area to inner lumen area is about 6:1. The through-holes that form the outlet ports are placed at 60° intervals around the elongate body at a constant spacing of 0.6 mm for every 180° of revolution (i.e., every three holes such that this is the distance between adjacent axially-aligned outlet ports). The spray pattern into air for this elongate body is shown in FIG. 3 and demonstrates a lack of uniform emission. For example, there are no visible fluid jets from the proximal-most 4 or 5 rows of holes.

Figure 23:
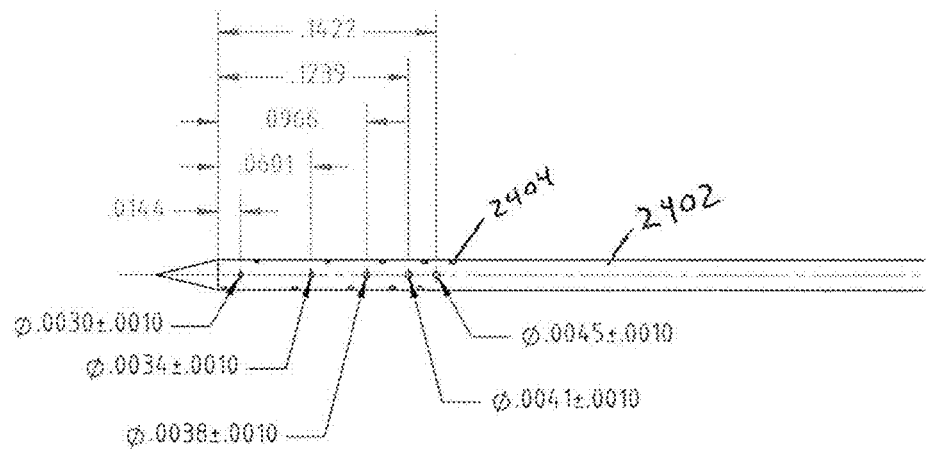
FIG. 23 is a side view of one embodiment of an elongate body according to the teachings of the present disclosure.
Figure 24:
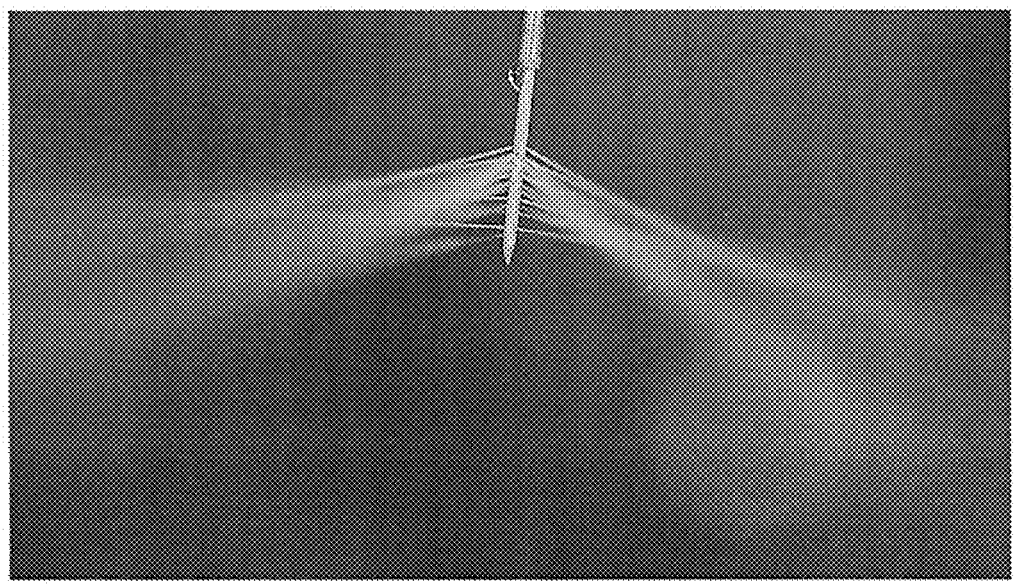
FIG. 24 is a photograph showing fluid flow in air for the elongate body of FIG. 22.

FIG. 23 illustrates a first embodiment of an elongate body 2402 according to the teachings described herein. The elongate body 2402 includes 15 through-holes, resulting in 30 total circular outlet ports 2404 that vary in diameter from 0.076 mm distally to 0.11 mm proximally. A resulting ratio of total outlet port area to inner lumen area is about 1.7:1. The through-holes that form the outlet ports are placed at 60° intervals around the elongate body and the spacing between adjacent aligned holes varies according to the specification shown in FIG. 23 (again, dimensions shown are in inches). More particularly, a distance between adjacent axially-aligned outlet ports increases from 0.46 mm to 1.16 mm as one moves from a proximal end of a fluid delivery portion of the elongate body to a distal end thereof. FIG. 24 depicts the spray of fluid (saline) into air for this elongate body at a flow rate of 35 ml/min. The spray pattern is clearly more uniform than that of the elongate body 2302 shown in FIG. 22. The figure also shows some variation in angle, likely due to residual axial momentum of the exiting fluid.

Figure 25:
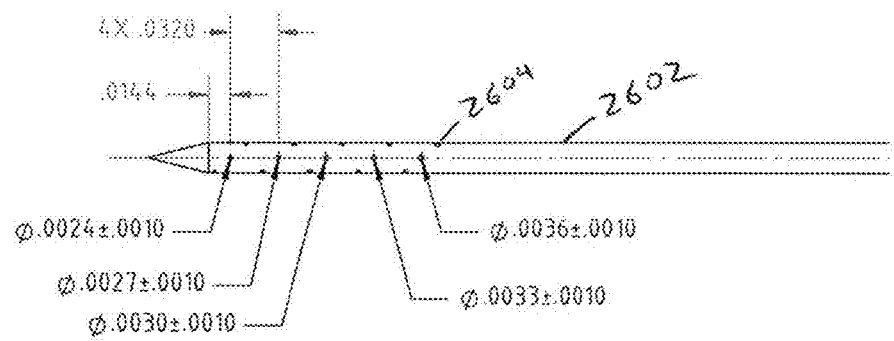
FIG. 25 is a side view of an alternative embodiment of an elongate body according to the teachings of the present disclosure.
Figure 26:
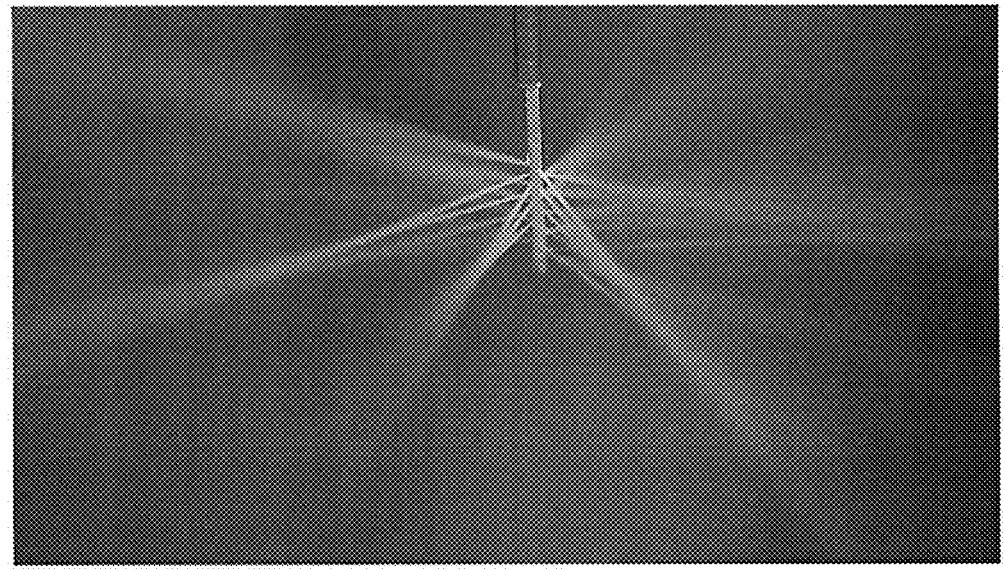
FIG. 26 is a photograph showing fluid flow in air for the elongate body of FIG. 24.

FIG. 25 illustrates a second embodiment of an elongate body 2602 according to the teachings described herein. The elongate body 2602 includes 15 through-holes, resulting in 30 total circular outlet ports 2604 that vary in diameter from 0.061 mm distally to 0.091 mm proximally. A resulting ratio of total outlet port area to inner lumen area is about 1.07:1. The through-holes that form the outlet ports are placed at 60° intervals around the elongate body at a constant spacing of 0.81 mm per 180° revolution (i.e., the spacing between axially-aligned outlet ports along a longitudinal axis of the elongate body is 0.81 mm—dimensions shown in the figure are in inches). FIG. 26 depicts the spray of fluid into air for this elongate body at a flow rate of 35 ml/min. The pattern exhibits uniform flow with small variations of jet angle between rows of outlet ports. The elongate body 2602 is referred to as the "M2" configuration in the data described below.

Figure 27:
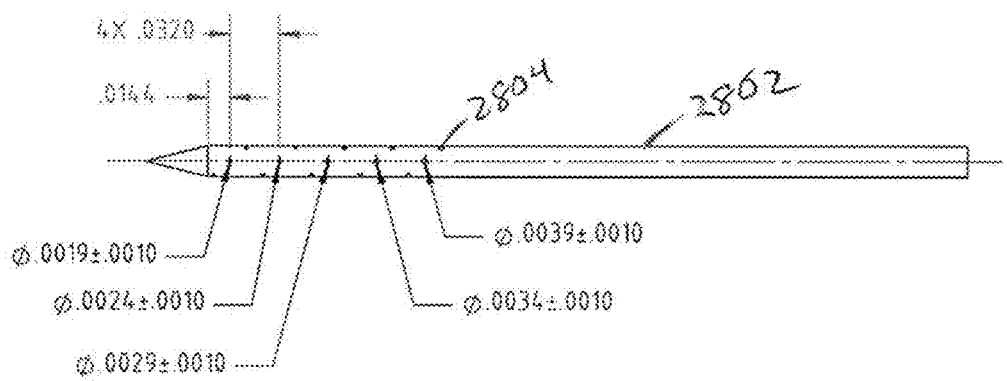
FIG. 27 is a side view of another embodiment of an elongate body according to the teachings of the present disclosure.
Figure 28:
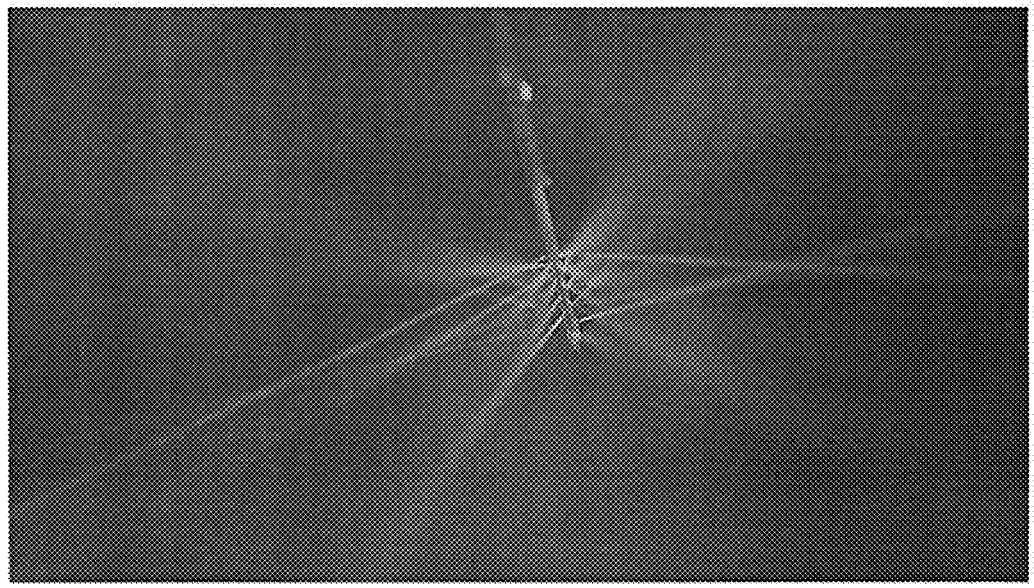
FIG. 28 is a photograph showing fluid flow in air for the elongate body of FIG. 26.

FIG. 27 illustrates a third embodiment of an elongate body 2802 according to the teachings described herein. The elongate body 2802 includes 15 through-holes, resulting in 30 total circular outlet ports 2804 that vary in diameter from 0.048 mm distally to 0.081 mm proximally (dimensions shown in the figure are in inches). A resulting ratio of total outlet port area to inner lumen area is about 1.04:1. The through-holes that form the outlet ports are placed at 60° intervals around the elongate body at a constant spacing of 0.81 mm per 180° revolution. FIG. 28 depicts the spray of fluid into air for this elongate body at a flow rate of 35 ml/min. The pattern exhibits uniform flow with small variations of jet angle between rows of outlet ports.

Figure 29:
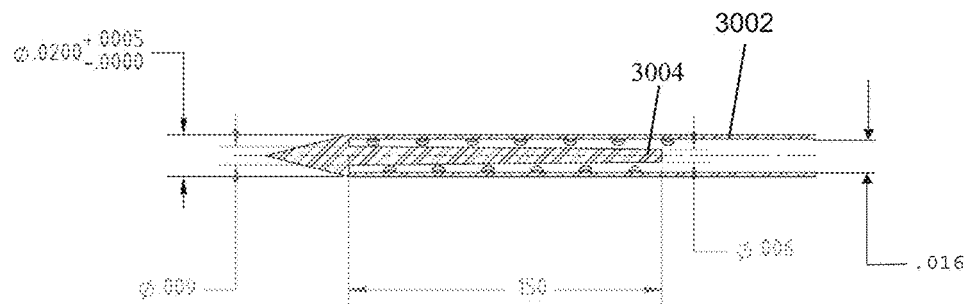
FIG. 29 is a side cross-sectional view of one embodiment of an elongate body including a flow diverter.

In addition to the elongate bodies described above, evaluations were conducted with the various elongate bodies including a flow diverter disposed in an inner lumen thereof. More particularly, the elongate bodies 2302, 2402, 2602, and 2802 were fitted with a cone-shaped tapered flow diverter pin along the center line of the elongate body. Exemplary dimensions of the flow diverter pin utilized are shown in FIG. 29, which depicts an elongate body 3002 that is the same as the elongate body 2302, but for the addition of the flow diverter 3004. In the data presented below, the elongate bodies including a flow diverter are referred to by their base configuration name plus the suffix "-FD," i.e., "O-FD," and "M2-FD."

Figure 30:
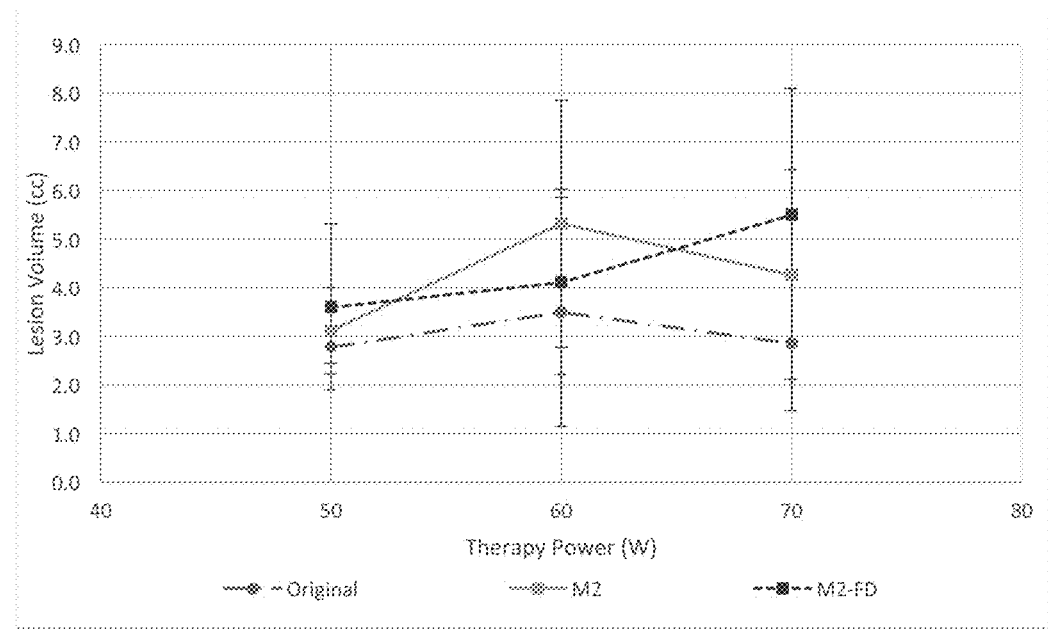
FIG. 30 is a plot of treated volume versus therapy power based on the experimental evaluations described herein.

Testing of the various configurations of the elongate bodies described above was conducted according to a protocol in which a fluid enhanced ablation therapy system of the type shown in FIG. 1 performed test ablations on bovine heart tissue immersed in a 37° C. saline bath. The ablation therapy parameters used are presented below in TABLE 1. Note the relatively high power levels and relatively low fluid flow rates, which create a challenging environment for the elongate body. During the procedure, impedance from the elongate body to a return electrode in the saline bath was monitored to detect any increases, which would indicate that the local tissue electrical resistance was increasing—something that makes control of the therapy more difficult. Following the test, the volume of treated tissue (referred to as a "lesion") created during each test ablation was determined. A tabulation of lesion size data is included in TABLE 2 and FIG. 30 shows a plot of lesion volume versus therapy power level for the original elongate body and selected embodiments of an elongate body according to the teachings of the present disclosure.

Table 1

TABLE 1

| Therapy Power (W) | Saline Temperature (° C.) | Saline Flow Rate (ml/min) | Therapy Duration (min:sec) |
|---|---|---|---|
| 50 | 60 | 5 | 1:00 |
| 60 | 60 | 5 | 1:00 |
| 70 | 60 | 5 | 1:00 |

TABLE 2

| Elongate Body Type | Power (W) | Saline Temperature (° C.) | Saline Flow Rate (mL/min) | Duration (sec) | N | Average Lesion Volume (cc) | StDev Lesion Volume (cc) | Average Max Dimension (cm) | StDev Max Dimension (cm) |
|---|---|---|---|---|---|---|---|---|---|
| Original | 50 | 60 | 5 | 60 | 5 | 2.79 | 0.35 | 1.80 | 0.19 |
| Original | 60 | 60 | 5 | 60 | 5 | 3.51 | 2.36 | 2.04 | 0.72 |
| Original | 70 | 60 | 5 | 60 | 5 | 2.86 | 1.38 | 2.10 | 0.42 |
| Original Combined | — | — | — | TOTAL | 15 | — | — | — | — |
| M2 | 50 | 60 | 5 | 60 | 5 | 3.12 | 0.89 | 2.22 | 0.41 |
| M2 | 60 | 60 | 5 | 60 | 5 | 5.33 | 2.54 | 2.30 | 0.23 |
| M2 | 70 | 60 | 5 | 60 | 6 | 4.27 | 2.15 | 2.22 | 0.31 |
| M2 Combined | — | — | — | TOTAL | 16 | — | — | — | — |
| M2-FD | 50 | 60 | 5 | 60 | 4 | 3.61 | 1.72 | 2.08 | 0.17 |
| M2-FD | 60 | 60 | 5 | 60 | 3 | 4.12 | 1.91 | 2.50 | 0.20 |
| M2-FD | 70 | 60 | 5 | 60 | 4 | 5.50 | 2.60 | 2.33 | 0.62 |
| M2-FD Combined | — | — | — | TOTAL | 11 | — | — | — | — |

As shown in the table and figure, utilizing an elongate body according to the teachings of the present disclosure can create generally larger volumes of treated tissue when compared to elongate bodies known in the art. This can include, for example, an alternative pattern of outlet ports that vary in size and spacing, the inclusion of a flow diverter in an inner lumen of the elongate body, or a combination thereof. For example, the inclusion of a flow diverter generally increased lesion volume, especially at higher power levels.

In addition, monitoring of impedance during the experimental therapies indicated that the elongate bodies described in the present disclosure experienced reduced mean therapy impedance when compared to elongate bodies known in the art. Similar to lesion size above, for example, the inclusion of a flow diverter reduced mean therapy impedance. The inclusion of alternative hole patterns with varying hole size and/or spacing according to the teachings provided herein also produced a reduction in mean therapy impedance.

Therapy impedance was also analyzed to determine which test ablations experienced a maximum therapy impedance below 100Ω, between 100 and 150Ω, and above 150Ω. These categories were selected based on prior investigation and generally represent best-, moderate-, and worst-case impedance conditions for consistent power delivery. Qualitatively speaking, the results show that the elongate body configurations disclosed herein provide improved therapy performance by maintaining lower impedance levels.

Figure 31:
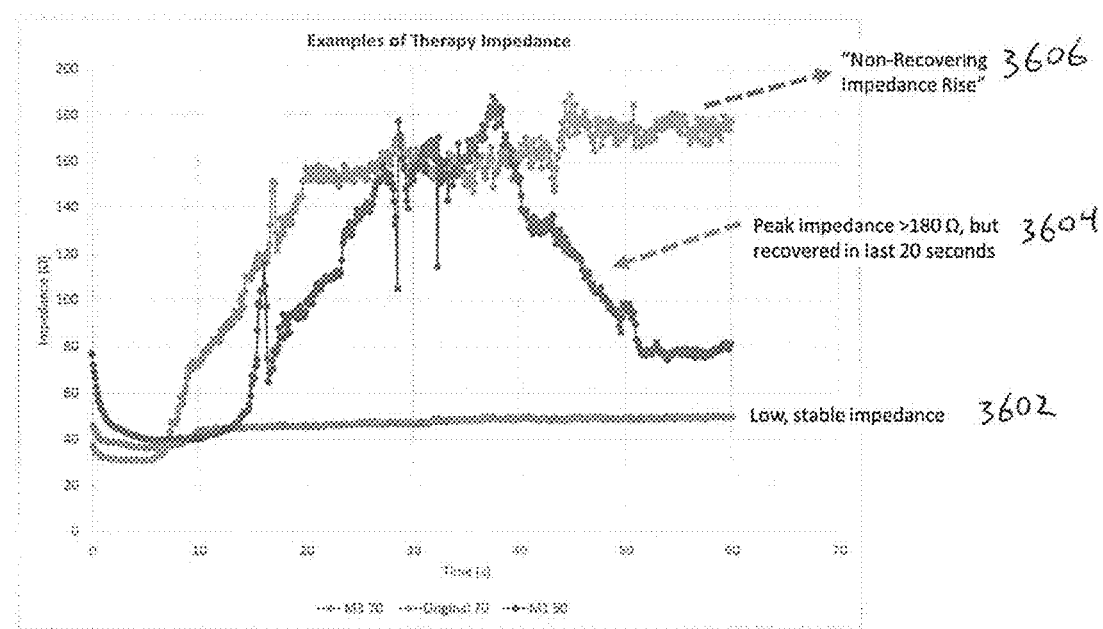
FIG. 31 is a plot of therapy impedance trends showing low, stable impedance, an impedance rise that recovers, and a non-recovering impedance rise.

In addition to analyzing maximum therapy impedance, an additional metric was calculated to determine if a non-recovering therapy impedance rise above 150Ω had occurred. Therapies performed above this impedance value typically end up being limited in the amount of power being delivered to tissue and therefore represent worst-case ablation conditions. In addition to indicating whether an ablation was power-limited, this metric can indicate whether the therapy impedance was contributing to a rise or a recovery. For purposes of this calculation, a non-recovering impedance rise was defined as a therapy impedance that either exceeded 200Ω, or an impedance that exceeded 150Ω and had at least one impedance measurement within 15Ω of maximum impedance during the final ten seconds of ablation time. FIG. 31 illustrates an example of three different therapy impedance trends exhibited during the experiments, including a low, stable impedance 3602, a recovering impedance rise above 150Ω 3604, and a non-recovering impedance rise about 150Ω 3606.

Figure 32:
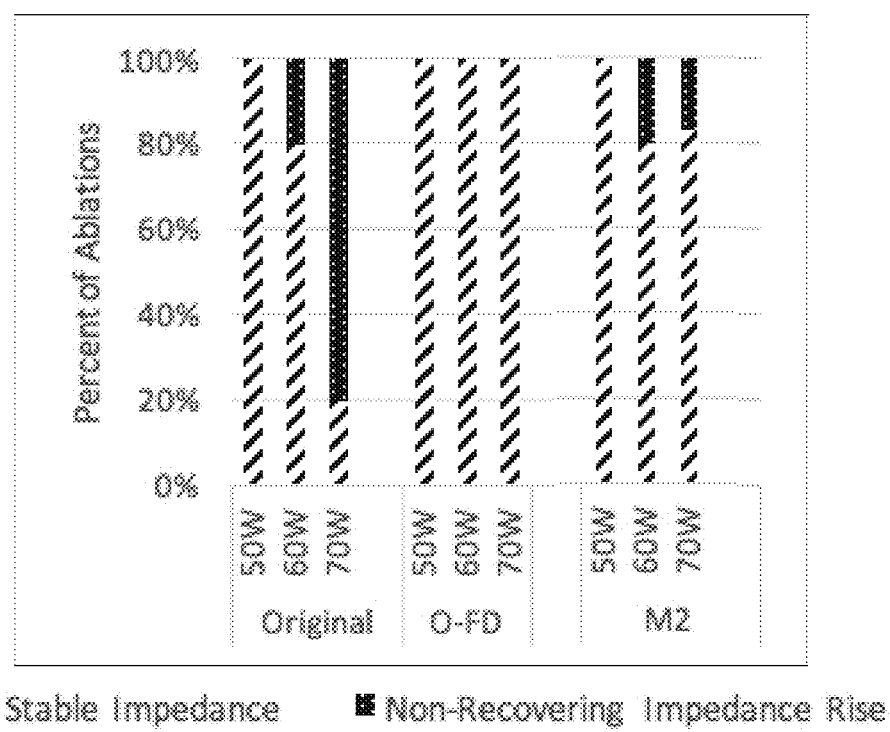
FIG. 32 is a plot of a rate of non-recovering impedance rise based on the experimental evaluations described herein.

FIG. 32 and TABLE 3 below present selected results from the experimental ablation tests of the percentage of ablations performed with non-recovering impedance rises. In general, the new elongate body configurations and/or the addition of a flow diverter feature perform better than the prior elongate body configuration.

TABLE 3

| Elongate Body | 50W | 60W | 70W | Overall |
|---|---|---|---|---|
| Original | 0.0% | 20.0% | 80.0% | 33.3% |
| M2 | 0.0% | 20.0% | 16.7% | 12.5% |
| O-FD | 0.0% | 0.0% | 0.0% | 0.0% |

As demonstrated by the results presented above, the "original" elongate body produced generally smaller lesions, by volume, than the elongate bodies constructed according to the teachings provided herein. For example, the "M2" elongate body consistently produced larger lesions than the "original" embodiment at every power setting. Accordingly, qualitatively speaking, the "M2" elongate body outperformed the "original" elongate body. The addition of a flow diverter to the "M2" elongate body improved performance further.

Moreover, the "M2" and other alternative elongate bodies exhibited generally lower therapy impedance than the "original" elongate body, particularly as the therapy power was increased. This could be one explanation for the differences in therapy lesion volume produced by the "M2" elongate body, as the lower impedance can allow more consistent power delivery that is unaffected by current or voltage limits.

A significant performance improvement exhibited by the new elongate body embodiment is shown in FIG. 31. As therapy power was increased to 60 W and 70 W, the rate of unrecoverable impedance rises increases dramatically for the "original" elongate body, while the new embodiments experience far less of an increase. Indeed, the rate of unrecoverable impedance remains below 20% for the "M2" and "O-FD" elongate bodies even at the highest power level. This decrease in runaway impedance is the result of better saline hydration of the surrounding tissue during therapy, which can be attributed to an improved flow pattern produced by the new elongate body hole pattern.

With regard to the addition of a flow diverter, the results of the experimental evaluation generally show improvements in therapy impedance and rate of non-recovering impedance rise. Any inconsistencies in the data may be attributable to the prototypes utilized, as tight tolerances are required for manufacture of these elongate bodies (e.g., to ensure that a flow diverter is centered within an inner lumen, etc.). Accordingly, data presented here should be considered more for its qualitative instruction regarding the performance comparison between an existing elongate body and the new embodiments described herein, and less for any quantitative comparison of the various embodiments. Taking such a qualitative view, the results show that the elongate body configurations disclosed herein (i.e., embodiments employing alternative hole patterns and sizes, as well as the inclusion of a flow diverter feature) produce larger lesions or volumes of treated tissue and exhibit lower impedance than elongate bodies known in the art.

All papers and publications cited herein are hereby incorporated by reference in their entirety. One skilled in the art will appreciate further features and advantages of the present disclosure based on the above-described embodiments. Accordingly, the present disclosure is not to be limited by what has been particularly shown and described, except as indicated by the appended claims.

What is claimed is:

1. An ablation device, comprising:
   an elongate body having an inner lumen;
   a plurality of outlet ports formed in the elongate body and disposed along a length thereof, the plurality of outlet ports being configured to deliver fluid from the inner lumen to tissue surrounding the elongate body;
   an ablation element configured to heat the tissue surrounding the elongate body;
   wherein a flow resistance of the elongate body increases along the length of the elongate body containing the plurality of outlet ports from a proximal end thereof to a distal end thereof; and
   wherein the elongate body includes tapered sidewalls that progressively increase in thickness from a proximal end to a distal end of the length of the elongate body containing the plurality of outlet ports.

2. The device of claim 1, wherein the flow resistance of the elongate body includes any of a flow resistance per unit length of inner lumen and a resistance to fluid flow from the lumen through the plurality of outlet ports.

3. The device of claim 1, wherein a ratio of a sum of an area of each of the plurality of outlet ports to an area of the inner lumen is less than about 3:1.

4. The device of claim 1, wherein the flow resistance to fluid flow through a distal 25% of the plurality of outlet ports is such that they deliver less than about 70% by volume of fluid delivered into tissue from the plurality of outlet ports.

5. The device of claim 1, wherein the flow resistance to fluid flow through a distal 25% of the plurality of outlet ports is such that they deliver less than about 55% by volume of fluid delivered into tissue from the plurality of outlet ports.

6. The device of claim 1, wherein the flow resistance to fluid flow through a distal 25% of the plurality of outlet ports is such that they deliver less than about 40% by volume of fluid delivered into tissue from the plurality of outlet ports.

7. The device of claim 1, wherein a cross-sectional area of each of the plurality of outlet ports decreases from a proximal end of the elongate body to a distal end of the elongate body.

8. The device of claim 1, wherein spacing between adjacent axially-aligned outlet ports increases from a proximal end of the elongate body to a distal end of the elongate body.

9. The device of claim 1, wherein at least one of the plurality of outlet ports has a non-circular shape.

10. The device of claim 1, wherein at least one of the plurality of outlet ports has a slot shape.

11. The device of claim 1, further comprising:
    a flow diverter disposed within the inner lumen of the elongate body along the length of the elongate body containing the plurality of outlet ports;
    wherein a diameter of the flow diverter increases from a proximal end thereof to a distal end thereof.

12. The device of claim 1, wherein the ablation element is a radio frequency electrode disposed along a length of the elongate body; and
    wherein the device includes at least one outlet port positioned at least partially beyond a boundary of the ablation element to deliver fluid to tissue immediately adjacent to the boundary of the ablation element.

13. The ablation device of claim 1, wherein at least a distal portion of the elongate body is configured to be inserted into tissue.

14. The ablation device of claim 1, wherein the elongate body includes a tissue-puncturing distal tip.

15. The ablation device of claim 14, wherein the tissue-puncturing distal tip is a pointed tip.

16. The ablation device of claim 1, further comprising a heating assembly disposed within the inner lumen of the elongate body that is configured to heat fluid as it passes through the inner lumen.

17. The ablation device of claim 16, wherein the heating assembly is disposed proximal to the plurality of outlet ports.

18. The device of claim 1, wherein the flow resistance to fluid flow through a distal 25% of the plurality of outlet ports is such that they deliver less than about 25% by volume of fluid delivered into tissue from the plurality of outlet ports.

19. The device of claim 1, wherein the flow resistance to fluid flow through a proximal 25% of the plurality of outlet ports is such that they deliver more than about 25% by volume of fluid delivered into tissue from the plurality of outlet ports.

* * * * *